(12) United States Patent
Tam et al.

(10) Patent No.: US 10,092,515 B2
(45) Date of Patent: *Oct. 9, 2018

(54) LIPOSOMAL FORMULATIONS OF POLYMYXIN B AND USES THEREOF

(71) Applicants: Vincent Tam, Bellaire, TX (US); Diana Chow, Houston, TX (US); Jie Gohlke, Houston, TX (US)

(72) Inventors: Vincent Tam, Bellaire, TX (US); Diana Chow, Houston, TX (US); Jie Gohlke, Houston, TX (US)

(73) Assignee: University of Houston System, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/817,800

(22) Filed: Nov. 20, 2017

(65) Prior Publication Data

US 2018/0071217 A1    Mar. 15, 2018

Related U.S. Application Data

(63) Continuation-in-part of application No. 13/899,753, filed on May 22, 2013, now Pat. No. 9,820,940.

(60) Provisional application No. 61/684,276, filed on Aug. 17, 2012.

(51) Int. Cl.
| | |
|---|---|
| *A61K 9/127* | (2006.01) |
| *A61K 9/00* | (2006.01) |
| *A61K 47/28* | (2006.01) |
| *A61K 47/24* | (2006.01) |
| *A61K 38/12* | (2006.01) |

(52) U.S. Cl.
CPC ............ *A61K 9/127* (2013.01); *A61K 9/0019* (2013.01); *A61K 38/12* (2013.01); *A61K 47/24* (2013.01); *A61K 47/28* (2013.01)

(58) Field of Classification Search
CPC ....................................................... A61K 9/127
See application file for complete search history.

(56) References Cited

U.S. PATENT DOCUMENTS

| | | | | |
|---|---|---|---|---|
| 5,269,979 | A * | 12/1993 | Fountain | A01N 25/04 264/4.1 |
| 5,759,571 | A * | 6/1998 | Hersch | A61K 9/127 424/450 |
| 6,613,352 | B2 * | 9/2003 | Lagace | A61K 9/127 264/4.1 |
| 2006/0073198 | A1 * | 4/2006 | Boni | A61K 9/0078 424/450 |
| 2009/0081733 | A1 * | 3/2009 | Doran-Peterson | C07K 7/62 435/71.1 |
| 2010/0292136 | A1 * | 11/2010 | Vaara | C07K 7/62 514/2.8 |

\* cited by examiner

*Primary Examiner* — Gollamudi Kishore
(74) *Attorney, Agent, or Firm* — Benjamin Aaron Adler

(57) ABSTRACT

The present invention provides an intravenous liposomal formulation of a low dose polymyxin B or a pharmaceutical composition thereof. The present invention also provides methods utilizing the intravenous liposomal formulation or its pharmaceutical composition for increasing the therapeutic efficacy during treatment of a bacterial infection in a subject, for decreasing exposure of renal tissue to the polymyxin B during a course of polymyxin B treatment and for lowering exposure to polymyxin B in renal tissues in a subject receiving polymyxin B treatment.

16 Claims, 8 Drawing Sheets

LIPOSOMAL FORMULATIONS OF POLYMYXIN B AND USES THEREOF

CROSS-REFERENCE TO RELATED APPLICATION

This application is a continuation-in-part under 35 U.S.C. § 120 of pending application U.S. Ser. No. 13/899,753, filed May 22, 2013, which claims benefit of priority under 35 U.S.C. § 119(e) of provisional application U.S. Ser. No. 61/684,276, filed Aug. 17, 2012, the entirety of both of which is hereby incorporated by reference.

FEDERAL FUNDING LEGEND

This invention was made with government support under Grant Number R15AI089671-01 awarded by the National Institutes of Health. The government has certain rights in the invention.

BACKGROUND OF THE INVENTION

Field of the Invention

The present invention is in the field of pharmacotherapy of Gram-negative bacterial infections. More specifically, the present invention is directed to intravenous liposomal formulations of low dose polymyxin B and uses thereof.

Description of the Related Art

Infections caused by multidrug-resistant (MDR) Gram-negative bacteria such as *Acinetobacter baumannii*, *Pseudomonas aeruginosa* and *Klebsiella pneumoniae* have presented a critical challenge to the world for decades (5, 7, 17). Among different infections caused by multidrug-resistant Gram-negative bacteria, pulmonary infections are especially problematic and are associated with the highest mortality rate (11, 15, 28). Since no first-line antibiotic is effective, polymyxin B is often used as the last resort treatment for infections caused by multidrug-resistant Gram-negative bacteria (19, 30).

Polymyxin B (USP) is commercially available as a mixture of several closely related polypeptides, obtained from cultures of various strains of *Bacillus polymyxa* and related species (24). The major components of polymyxin B (USP) are polymyxin B1, B2, B3 and isoleucine-B1 (PB1, PB2, PB3 and ile-PB1(23); the proportions of which are 73.5%, 13.7%, 4.2% and 8.6%, respectively (14).

Most clinical isolates of Gram-negative bacilli, including those that are multidrug-resistant, are susceptible to polymyxin B (6, 13, 26). Intravenous polymyxin B sulfate (USP) is commonly used for the treatment of critically ill patients with pulmonary infections (12). Despite good in vitro susceptibility, previous studies demonstrated that polymyxin B was associated with reduced efficacy in the treatment of pulmonary infections (12, 16, 27). A possible explanation for poor therapeutic outcomes is limited penetration of polymyxin B into the site of infection, i.e., the epithelial lining fluid (ELF).

Liposomes are microscopic spheres which were developed as drug delivery vehicles/systems in the 1980s. The first liposome-based pharmaceuticals were approved for commercial use in the 1990s. Liposomes are considered a promising drug delivery system since they passively target tumor tissue by using the pathophysiological characteristics of solid tumors such as hyperplasia and increased vascular permeability, but also a defect in lymphatic drainage. These features facilitate extravasation of nanoparticles and the liposomes can be retained in the tissue for longer time due to the enhanced permeability and retention effect (EPR). Thus, liposome encapsulation could potentially alter the pharmacokinetics and biodistributions of antimicrobials, compared with standard formulations (2, 10). Increased uptake by activated tissue macrophages would allow higher antimicrobial concentrations to be achieved in pulmonary tissues (4, 8) and presumably improve treatment efficacy.

Nephrotoxicity is the major concern hindering considerable dose escalation to circumvent poor concentration achieved in the epithelial lining fluid. Reduced drug uptake into the kidneys would decrease or delay injury to the kidneys. Thus, there is a recognized need in the art for improved formulations of polymyxin. Specifically, the prior art is deficient in the lack of liposomal formulations of polymyxin that enhance drug delivery to the site of an infection susceptible to the polymyxin. The present invention fulfills this longstanding need and desire in the art.

SUMMARY OF THE INVENTION

The present invention is directed to an intravenous liposomal formulation. The formulation consists of unilamellar vesicles each composed of lipid components dipalmitoylphosphatidylcholine and at least one of cholesterol, α-tocopherol, or phosphatidylserine. The vesicle size is of about 714 nm to about 1372 nm. The formulation also consists of a low dose of polymyxin B encapsulated in the vesicles at a weight ratio of polymyxin B to the lipid components of about 1:20 to about 1:2. The intravenous liposomal formulation is useful for delaying the onset of nephrotoxicity.

The present invention also is directed to a pharmaceutical composition of the intravenous liposomal formulation which, in addition to the formulation, comprises an intravenously acceptable excipient.

The present invention is directed further to a method for increasing the therapeutic efficacy during treatment of a bacterial infection in a subject. The method comprises administering to the subject an amount of the intravenous liposomal formulation described herein which is effective to decrease exposure of renal tissue to the polymyxin B during the treatment.

The present invention is directed further still to a method for lowering exposure to polymyxin B in renal tissues in a subject during a course of polymyxin B treatment. The method comprises administering to the subject the pharmaceutical composition comprising the intravenous liposomal formulation described herein. The low dose of polymyxin B in the pharmaceutical composition correlates to a low concentration of the polymyxin B in the renal tissues after administration, thereby lowering exposure during the course of treatment.

The present invention is directed further still to a method for delaying onset of nephrotoxicity in a subject receiving treatment with polymyxin B. The method comprises administering to the subject pharmacological amounts of an intravenous liposomal formulation comprising a low dosage of polymyxin B or pharmaceutical composition thereof effective to delay the onset of nephrotoxicity in the subject.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 7A shows the Electron microscopic images of ultrathin kidney sections: control, at 3 h; with maleate treatment, at 3 h (FIG. 7B); with maleate treatment, at 14 days (FIG. 7C). No significant changes were noted in the control kidney. Specifically, the proximal tubular cells displayed intact microvilli (Vil) and mitochondria (Mi) of normal size, shape, and density. A few microvesicles/lysosomes (Ly) were noted. FIG. 7B shows marked changes were noted in proximal tubular cells of an experimental animal, including degenerative changes of individual tubular cells (lower right), multifocal disruption or loss of microvilli (Vil), abundant mitochondria (Mi) of variable sizes and shapes, and multiple dilated microvesicles (Mv). There were no significant changes in glomeruli, blood vessels, or other types of renal tubules. FIG. 7C shows proximal tubular cells displaying normal features, including intact microvilli (Vil), normal mitochondria (Mi), and few lysosomes (Ly). Original magnification, ×10,000 for all panels.

DETAILED DESCRIPTION OF THE PRESENT INVENTION

Figure 1A:
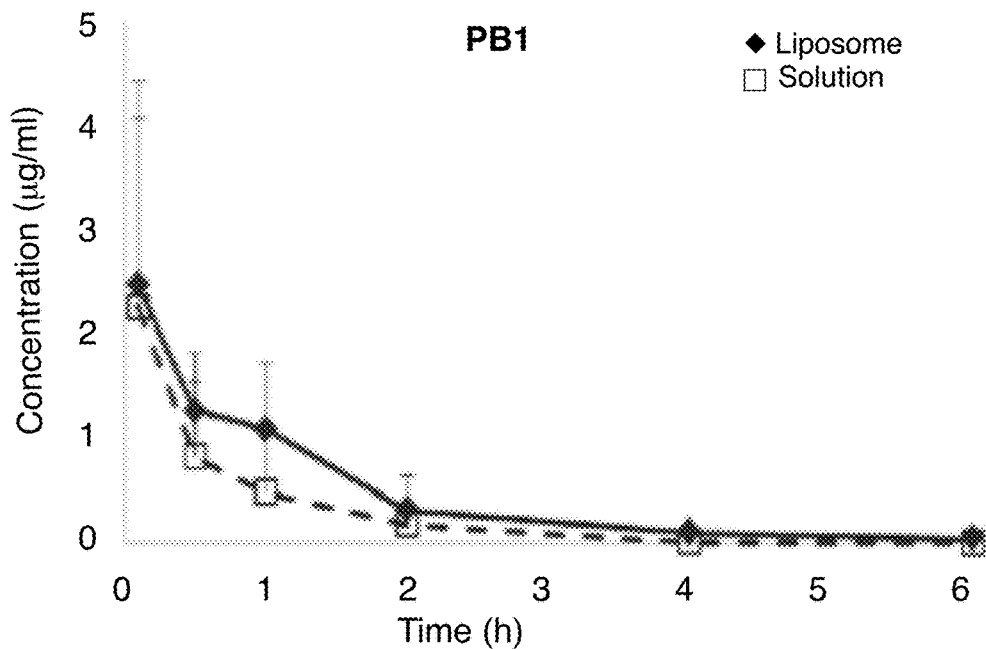
FIGS. 1A-1D show serum concentrations of polymyxin B1 (PB1) (FIG. 1A), polymyxin B2 (PB2) (FIG. 1B), polymyxin B3 (PB3) (FIG. 1C), and isoleucine B1 (ile-PB1) (FIG. 1D) after an intravenous administration of polymyxin B liposomes (diamonds) and aqueous solution (USP) (squares). N=4, data shown as mean±SD. Drug exposures were normalized by the dose.
Figure 1B:
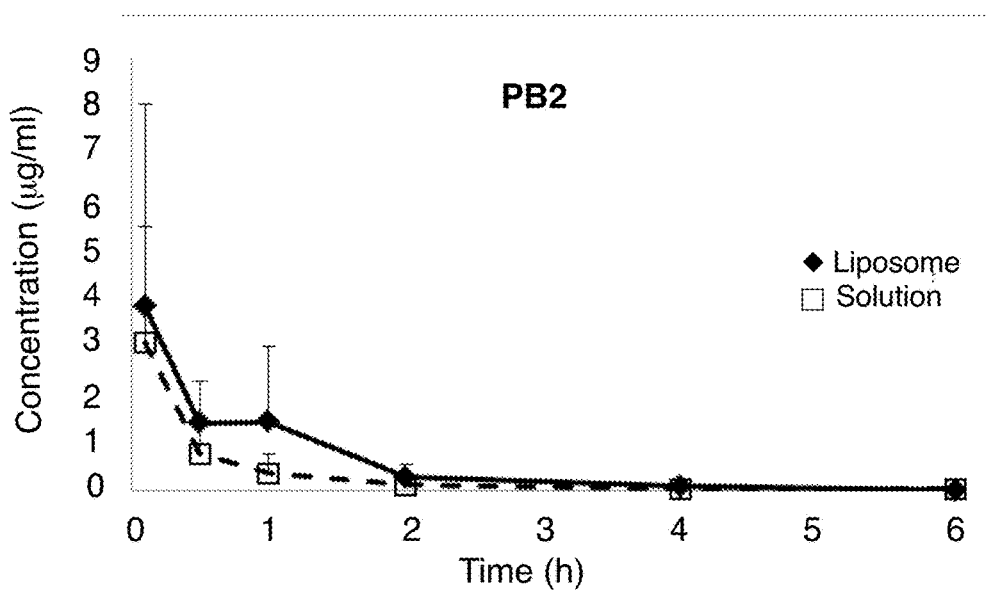
Figure 1C:
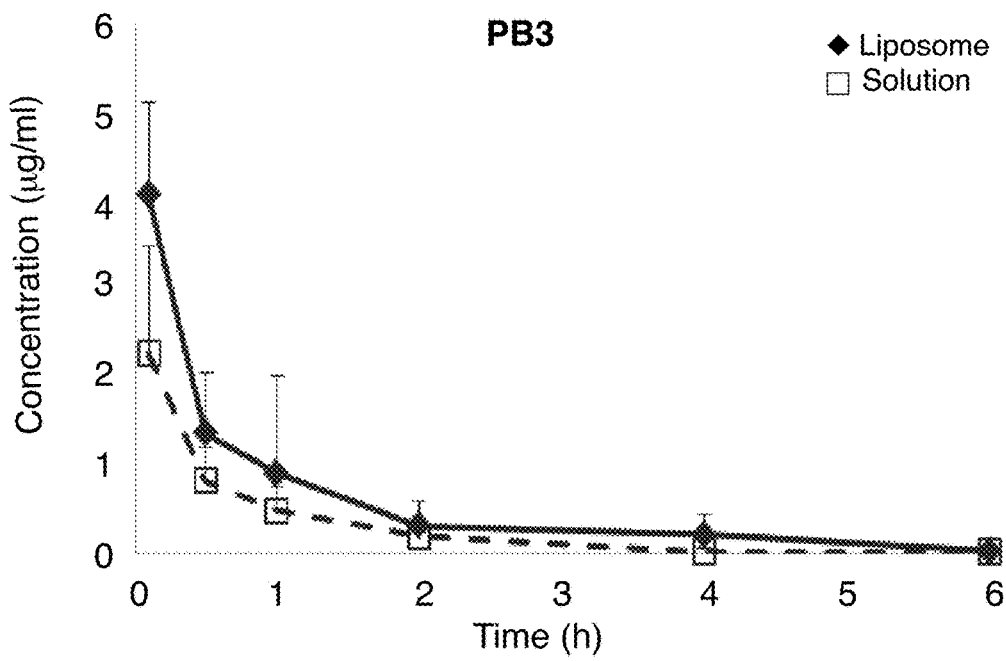
Figure 1D:
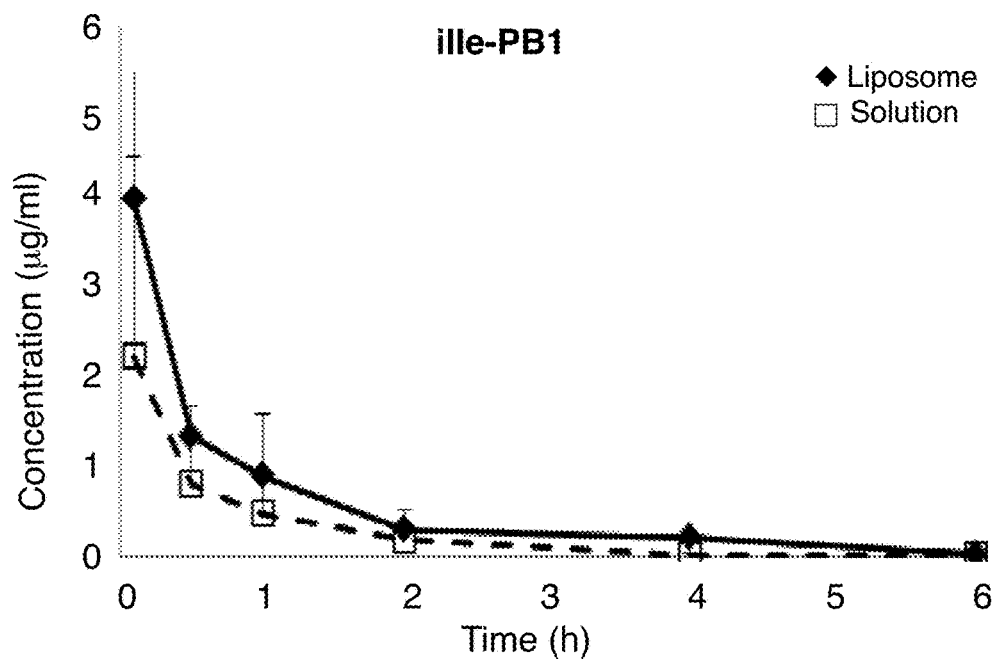
Figure 2A:
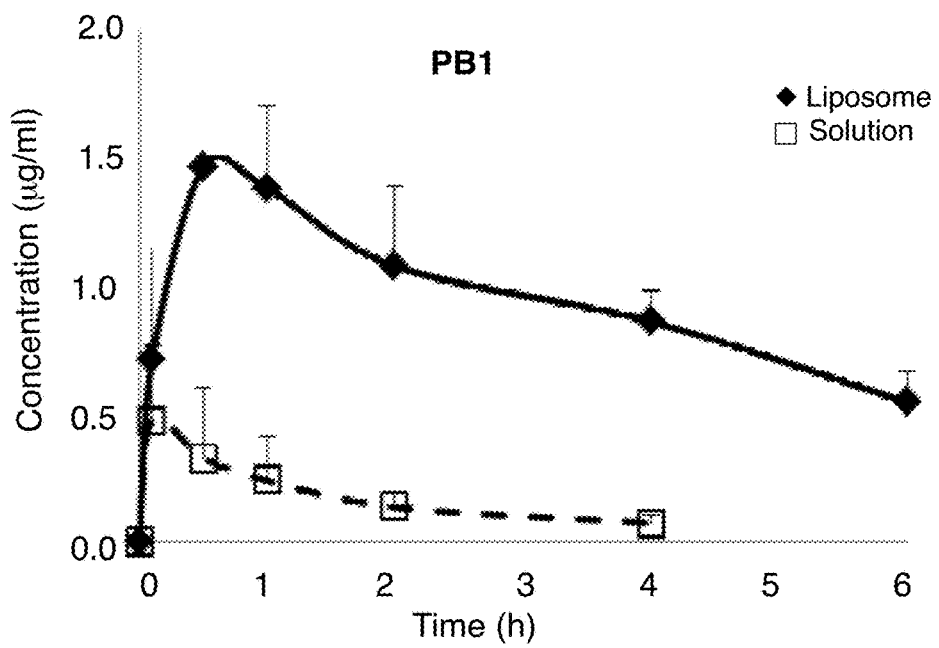
FIGS. 2A-2D show epithelial lining fluid concentrations of polymyxin B1 (PB1) (FIG. 2A), polymyxin B2 (PB2) (FIG. 2B), polymyxin B3 (PB3) (FIG. 2C), and isoleucine B1 (ile-PB1) (FIG. 2D) after an intravenous administration of polymyxin B liposomes (diamonds) and aqueous solution (USP) (squares). N=4, data shown as mean±SD. Drug exposures were normalized by the dose.
Figure 2B:
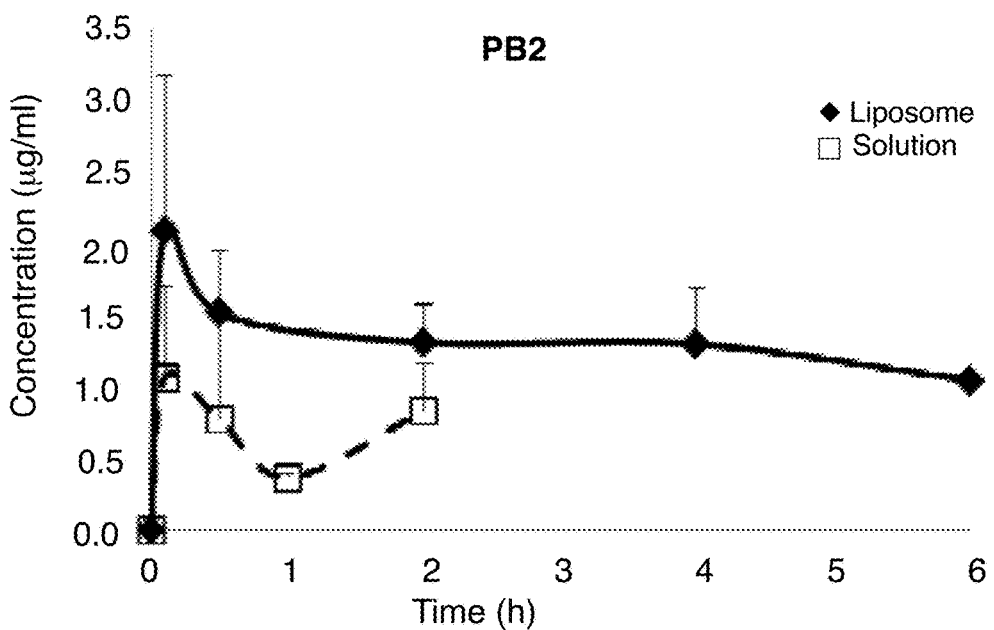
Figure 2C:
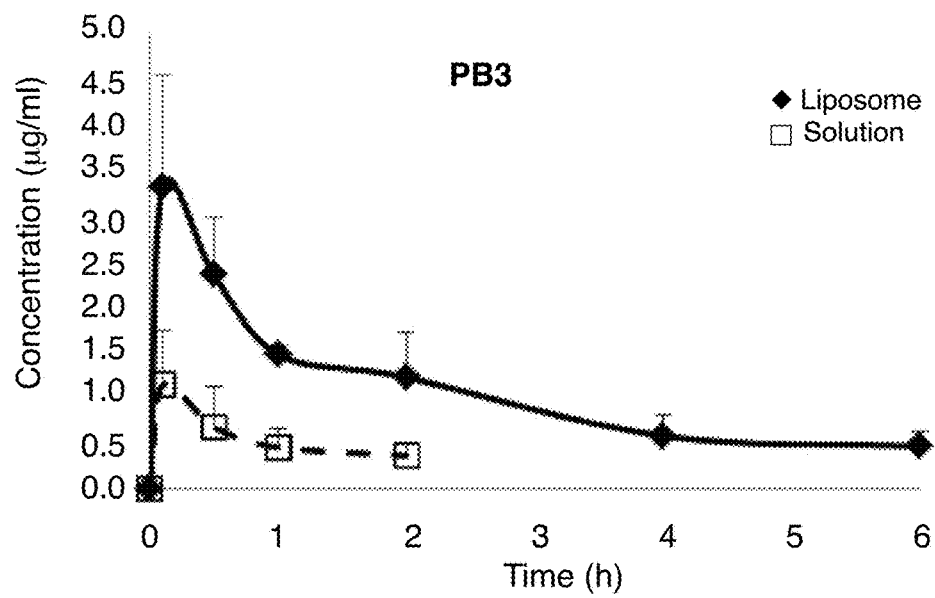
Figure 2D:
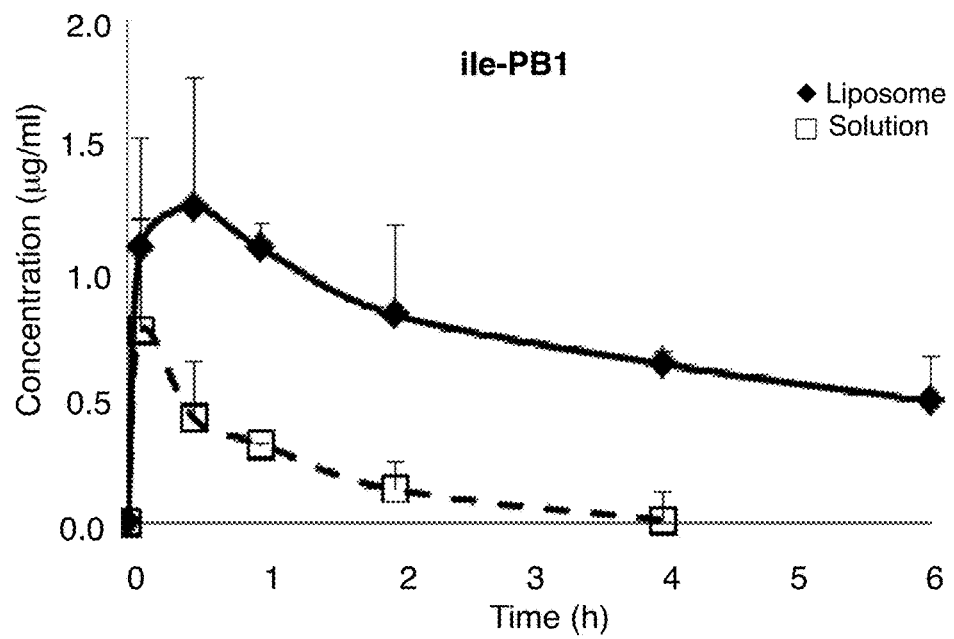

For convenience, before further description of the present invention, certain terms employed in the specification, examples and appended claims are collected herein. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, components, method steps, and/or methods of the invention. It is contemplated that any composition, component or method described herein can be implemented with respect to any other composition, component or method described herein.

The term "or" in the claims refers to "and/or" unless explicitly indicated to refer to alternatives only or the alternatives are mutually exclusive, although the disclosure supports a definition that refers to only alternatives and "and/or".

The terms "comprise" and "comprising" are used in the inclusive, open sense, meaning that additional elements may be included.

The term "including" is used herein to mean "including, but not limited to". "Including" and "including but not limited to" are used interchangeably.

The term "about" is used herein to refer to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

The term "liposome or liposomes" is art-recognized and refers generally to microscopic spheres that have three distinct compartments that can be used to carry various compounds, for example, drugs. A liposome has 1) an interior aqueous compartment; 2) a hydrophobic bilayer; and 3) a polar inter-phase of the inner and outer leaflet. Depending on the chemical nature of the compound to be encapsulated it is localized to one of the compartments.

The term "lipid-based composition" as used herein refers to compositions that primarily comprise lipids. Non-limiting examples of lipid-based compositions may take the form of coated lipid particles, liposomes, emulsions, micelles, and the like.

The term "antibacterial" is art-recognized and refers to the ability of the compounds of the present invention to prevent, inhibit or destroy the growth of microbes of bacteria.

The terms "antiinfective" and "antiinfective agent" are used interchangeably throughout the specification to describe a biologically active agent which can kill or inhibit the growth of certain other harmful pathogenic organisms, including but not limited to bacteria, yeasts and fungi, viruses, protozoa or parasites, and which can be administered to living organisms, especially animals such as mammals, particularly humans.

The term "antimicrobial" is art-recognized and refers to the ability of the compounds of the present invention to prevent, inhibit or destroy the growth of microbes such as bacteria, fungi, protozoa and viruses.

The terms "bioavailable" or "bioavailability" are art-recognized and refer to a form of the subject invention that allows for it, or a portion of the amount administered, to be absorbed by, incorporated to, or otherwise physiologically available to a subject or patient to whom it is administered.

A "patient," "subject" or "host" to be treated by the subject method may mean either a human or non-human animal.

The term "mammal" or "subject" is known in the art, and exemplary mammals include humans, primates, bovines, porcines, canines, felines, and rodents, e.g., mice and rats.

The term "microbe" is art-recognized and refers to a microscopic organism. In certain embodiments the term microbe is applied to bacteria. In other embodiments the term refers to pathogenic forms of a microscopic organism.

The term "pharmaceutically-acceptable salts" is art-recognized and refers to the relatively non-toxic, inorganic and organic acid addition salts of compounds, including, for example, those contained in compositions of the present invention.

The term "prodrug" is art-recognized and is intended to encompass compounds which, under physiological conditions, are converted into the antibacterial agents of the present invention. A common method for making a prodrug is to select moieties which are hydrolyzed under physiological conditions to provide the desired compound. In other embodiments, the prodrug is converted by an enzymatic activity of the host animal or the target bacteria.

The term "illness" as used herein refers to any illness caused by or related to infection by an organism.

The terms "treating" or "treatment" are art-recognized and refer to curing as well as ameliorating at least one symptom of any condition or disease or illness.

Agents of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

In one embodiment of the present invention there is provided an intravenous liposomal formulation, consisting of unilamellar vesicles each composed of lipid components dipalmitoylphosphatidylcholine and at least one of cholesterol, α-tocopherol, or phosphatidylserine at a vesicle size of about 714 nm to about 1372 nm; and low dose of polymyxin B encapsulated in said vesicles at a weight ratio of polymyxin B to the lipid components of about 1:20 to about 1:2; for delaying onset of nephrotoxicity. In this embodiment, the polymyxin B dose is about 1 mg/kg to about 4 mg/kg.

In a related embodiment, there is provided a pharmaceutical composition comprising the intravenous liposomal formulation as described supra and an intravenously acceptable excipient.

In another embodiment of the present invention there is provided a method for increasing the therapeutic efficacy during treatment of a bacterial infection in a subject, comprising administering to the subject an amount of the intravenous liposomal formulation described supra effective to decrease exposure of renal tissue to the polymyxin B during the treatment. In addition, administering to the subject an amount of the intravenous liposomal formulation delays the onset of nephrotoxicity.

Also in this embodiments the bacterial infection may be caused by *Pseudomonas aeruginosa, Acinetobacter baumannii, Klebsiella pneumoniae, Bacillus anthracis, Listeria monocytogenes, Staphylococcus aureus, Salmenellosis, Yersina pestis, Mycobacterium leprae, Mycobacterium africanum, Mycobacterium asiaticum, Mycobacterium aviuin-intracellulaire, Mycobacterium chelonei abscessus, Mycobacterium fallax, Mycobacterium fortuitum, Mycobacterium kansasii, Mycobacterium leprae, Mycobacterium malmoense, Mycobacterium shimoidei, Mycobacterium simiae, Mycobacterium szulgai, Mycobacterium xenopi, Mycobacterium tuberculosis, Brucella melitensis, Brucella suis, Brucella abortus, Brucella canis, Legionella pneumonophilia, Francisella tularensis, Pneumocystis carinii, mycoplasma*, or *Burkholderia cepacia*. Particularly, the bacterial infection may be caused by multiple drug resistant *Pseudomonas aeruginosa, Acinetobacter baumannii*, or *Klebsiella pneumoniae*.

In yet another embodiment of the present invention there is provided a method for lowering exposure to polymyxin B in renal tissues in a subject during a course of polymyxin B treatment, comprising the step of administering to the subject the pharmaceutical composition comprising the intravenous liposomal formulation as described supra and an intravenously acceptable excipient, wherein the low dosage of polymyxin B in the pharmaceutical composition correlates to a low concentration of the polymyxin B in the renal tissues after administration, thereby lowering exposure during the course of treatment.

Also in this embodiments lowering exposure to polymyxin B in renal tissues correlates to delaying onset of nephrotoxicity in the subject. Further to this embodiments the course of polymyxin B treatment may be against a bacterial infection caused by *Pseudomonas aeruginosa, Acinetobacter baumannii, Klebsiella pneumoniae, Bacillus anthracis, Listeria monocytogenes, Staphylococcus aureus, Salmenellosis, Yersina pestis, Mycobacterium leprae, Mycobacterium africanum, Mycobacterium asiaticum, Mycobacterium aviuin-intracellulaire, Mycobacterium chelonei abscessus, Mycobacterium fallax, Mycobacterium fortuitum, Mycobacterium kansasii, Mycobacterium leprae, Mycobacterium malmoense, Mycobacterium shimoidei, Mycobacterium simiae, Mycobacterium szulgai, Mycobacterium xenopi, Mycobacterium tuberculosis, Brucella melitensis, Brucella suis, Brucella abortus, Brucella canis, Legionella pneumonophilia, Francisella tularensis, Pneumocystis carinii, mycoplasma*, and *Burkholderia cepacia*. Particularly, the course of polymyxin B treatment may be against a bacterial infection caused by multiple drug resistant bacteria. Representative examples are *Pseudomonas aeruginosa, Acinetobacter baumannii*, or *Klebsiella pneumoniae*.

In yet another embodiment of the present invention there is provided a method for delaying onset of nephrotoxicity in a subject receiving treatment with polymyxin B, comprising the step of administering to the subject pharmacological amounts of an intravenous liposomal formulation comprising a low dose of polymyxin B or pharmaceutical composition thereof effective to delay the onset of nephrotoxicity in the subject. In addition, delaying onset of nephrotoxicity in the subject correlates to lowering exposure to polymyxin B in renal tissues.

Also in this embodiment the intravenous liposomal formulation may consist of unilamellar vesicles each composed of lipid components dipalmitoylphosphatidylcholine and at least one of cholesterol, α-tocopherol, or phosphatidylserine at a vesicle size of about 714 nm to about 1372 nm; and the low dose of polymyxin B encapsulated in the vesicles at a weight ratio of polymyxin B to the lipid components of about 1:20 to about 1:2; for delaying onset of nephrotoxicity. Particularly, the low dose of polymyxin B may be about 1 mg/kg to about 4 mg/kg.

In addition in this embodiment the treatment with polymyxin B may treat a bacterial infection caused by *Pseudomonas aeruginosa, Acinetobacter baumannii, Klebsiella pneumoniae, Bacillus anthracis, Listeria monocytogenes, Staphylococcus aureus, Salmenellosis, Yersina pestis, Mycobacterium leprae, Mycobacterium africanum, Mycobacterium asiaticum, Mycobacterium aviuin-intracellulaire, Mycobacterium chelonei abscessus, Mycobacterium fallax, Mycobacterium fortuitum, Mycobacterium kansasii, Mycobacterium leprae, Mycobacterium malmoense, Mycobacterium shimoidei, Mycobacterium simiae, Mycobacterium szulgai, Mycobacterium xenopi, Mycobacterium tuberculosis, Brucella melitensis, Brucella suis, Brucella abortus, Brucella canis, Legionella pneumonophilia, Francisella tularensis, Pneumocystis carinii, mycoplasma,* and *Burkholderia cepacia*. Particularly the treatment with polymyxin B treats a bacterial infection caused by multiple drug resistant bacteria. Representative examples are *Pseudomonas aeruginosa, Acinetobacter baumannii*, or *Klebsiella pneumoniae*.

In yet another embodiment of the present invention, there is provided a liposomal formulation comprising a lipid component formed as vesicles each having a minimum size of at least 500 nm and a polymyxin encapsulated in the vesicles. In this embodiment the minimum size may be about 600 nm to about 1,750 nm. Also the vesicles may be a mixture of multilamellar vesicles and unilamellar vesicles. In addition in this embodiment the lipid component may comprise at least one of phosphatidyl choline, cholesterol, alpha-tocopherol, dipalmitoyl phosphatidyl choline, or phosphatidyl serine. For example, the lipid component may comprise dipalmitoyl phosphatidylcholine or cholesterol or a combination thereof. Furthermore, the polymyxin may be selected from the group consisting of polymyxin B1, polymyxin B2, polymyxin B3, polymyxin E1 and polymyxin E2. Further still a weight ratio of the polymyxin to the lipid component may be about 1:20 to about 1:2 and the polymyxin concentration in the formulation may be about 0.5 mg/ml to about 4 mg/ml.

In a related embodiment there is provided a pharmaceutical composition comprising the liposomal formulation described herein and an intravenously acceptable excipient. Such acceptable excipients are well-known and described further herein.

In yet another embodiment of the present invention, there is provided a method of treating a bacterial infection in a subject in need of such treatment, comprising: administering to the subject an effective amount of a liposomal formulation, comprising polymyxin; and a lipid component, wherein said formulation comprises vesicles having a size of about at least 500 nm. In this embodiment the bacteria causing the infection are as described supra and particularly may be a multiple drug resistant *Pseudomonas aeruginosa, Acinetobacter baumannii*, or *Klebsiella pneumoniae*.

In yet another embodiment of the present invention, there is provided a drug delivery system comprising a plurality of liposomes encapsulating a polymyxin therein, where the liposomes have a minimum vesicular size of at least 500 nm. Further to this embodiment the drug delivery system comprises a pharmaceutically acceptable excipient suitable for intravenous delivery. In this embodiment the plurality of liposomes may comprise those lipids singly or in combination that form as vesicles and have a minimum size and uni- and/or multilamellar structure as described for the liposomal formulations. Furthermore, the plurality of liposomes may encapsulate the polymyxin as described in those weight ratios and concentrations, also as described.

In yet another embodiment of the present invention, there is provided a method for increasing efficacy of a treatment for a bacterial infection in a subject in need of such treatment, comprising the step of delivering, intravenously, to the subject, the liposome-encapsulated polymyxin comprising the drug delivery system described herein, where the liposomes increase bioavailability and distribution of the polymyxin within the subject, thereby increasing efficacy of the treatment. In this embodiment the bacterial infection may be a pulmonary infection, such as, but not limited to, a pneumonia. Particularly, the infective agent may be a multiple drug resistant gram-negative bacteria, for example, a multidrug resistant *Pseudomonas aeruginosa, Acinetobacter baumannii*, or *Klebsiella pneumoniae*.

Polymyxin B (PB) is increasingly used as the last treatment for multidrug resistant (MDR) Gram-negative bacterial infections. In the present invention, the epithelial lining fluid (ELF) pharmacokinetics and efficacy of a Polymyxin B liposomal formulation were demonstrated. Two groups of Swiss Webster mice were intravenously administrated Polymyxin B liposomes, and aqueous solution, respectively, at approximately 3 mg/kg. Serial serum and epithelial lining fluid samples were collected for up to 6 hours to quantify the major Polymyxin B components.

Treatment efficacy of the liposomal formulation was evaluated in a neutropenic murine pneumonia model. Three groups of neutropenic mice (n=6) were infected by a clinical multiple drug resistant strain (*Pseudomonas aeruginosa* 9019), followed by intravenous administration of polymyxin B liposomes, sham liposomes and aqueous solution, respectively, at 3 mg/kg every 6 hours. Bacterial burden in animal lung tissues was quantified after 24 hours of therapy and compared using 1-way analysis of variance and survival over time was evaluated.

Compared with aqueous solution, the liposomal formulation was shown to have a slower rate of total clearance (PB1, 0.6±0.3 vs. 1.4±0.5 l/h/kg). The AUC ratio in the epithelial lining fluid between liposome and aqueous solution group ranged from 4.6 to 11.1 for various major polymyxin B components. In the efficacy study, a significantly lower bacterial burden was seen in the liposomal group (3.8±0.7 vs. 7.9±0.8 $Log_{10}$ CFU/g in solution group). Treatment with a polymyxin B liposomal formulation yielded higher penetration into pulmonary epithelial lining fluid, which resulted in superior efficacy and reduced residence in the kidneys.

Also a correlation between dose, renal drug exposure, and onset of polymyxin B-induced nephrotoxicity is demonstrated herein and provides insights into the role of megalin in renal accumulation of polymyxin B. It is contemplated that megalin is a promising target for designing pharmacological interventions to alleviate polymyxin B-induced nephrotoxicity.

In the present invention, polymyxin B was encapsulated in liposomes by a modified method of reversed-phase evaporation, followed by an extrusion. Serum and epithelial lining fluid pharmacokinetic profiles were compared between liposomal formulation and standard aqueous solution in mice. In addition, treatment efficacy was evaluated in a neutropenic murine pneumonia model of *Pseudomonas aeruginosa*. Improving drug delivery to the site of infection enhanced the effectiveness of polymyxin B for pulmonary infections caused by MDR Gram-negative bacteria.

Representative polymyxin chemical variants include but are not limited to polymyxin B and its components (e.g., B1, B2, B3, etc.) as well used for other related compounds, e.g., polymyxin E1, E2, etc. A person having ordinary skill in this art would also recognize that one could apply the teachings of the present invention to other related chemical compounds with similar physical-chemical properties to polymyxins. One example of a similar physical-chemical property to polymyxins is to be a highly polar cation. For example, the teachings of the present invention may be applied to the aminoglycosides such as, gentamicin, amikacin, tobramycin. Alternatively, a prodrug comprising a suitable antiinfective, antibacterial or antimicrobial agent may be encapsulated within the liposome or liposomal vesicles.

It is specifically contemplated that size is a critical aspect of the efficacy of the formulations described herein such that a minimum particle or vesicle size of the liposomes must be at least about 500 nm. As would be readily recognized by a person having ordinary skill in this art, liposome size is controlled by the preparation conditions (e.g., amount of ingredients used, temperature, pressure, duration, etc.). Useful formulations can comprise vesicles having a size of about 500 nm ranging to 2000 nm, e.g., at least 600 nm, at least 800 nm, at least 1000 nm, at least 1200 nm, at least 1500 nm, at least 1,750 nm, etc.

Generally, representative lipid components of the formulation include, but are not limited to one of or a combination of phosphatidylcholine, cholesterol, alpha-tocopherol, dipalmitoylphosphatidyl choline and phosphatidyl serine. The formulation of the present invention may comprise liposomes that are multilamellar vesicles, unilamellar vesicles or mixtures of multilamellar vesicles and unilamellar vesicles. In one preferred aspect, the lipid component comprises dipalmitoyl phosphatidylcholine (DPPC). In another preferred aspect of this formulation, the lipid component comprises cholesterol. In yet another preferred aspect of this formulation, the lipid component comprises dipalmitoyl phosphatidylcholine and cholesterol. Generally, the polymyxin concentration of the formulation is in a range of from about 0.5 mg/ml to about 4 mg/ml. Typically, the formulation of the present invention contains the weight ratio of the polymyxin to the lipid component is in the range of from about 1:20 to about 1:2.

As would be readily recognized by a person having ordinary skill in this art, liposome size is controlled by the preparation conditions (e.g., amount of ingredients used, temperature, pressure, duration, etc.). It is contemplated that useful formulations can comprise vesicles having a size of about 500-2000 nm, e.g., at least 750 nm, at least 1000 nm, at least 1250 nm, at least 1500 nm, at least 1,750 nm, etc. Generally, representative lipid components of said formulation include but are not limited to a compound selected from the group consisting of phosphatidylcholine, cholesterol, alpha-tocopherol, dipalmitoylphosphatidyl choline and phosphatidyl serine. The formulation of the present invention may comprise liposomes that are multilamellar vesicles, unilamellar vesicles or mixtures of multilamellar vesicles and unilamellar vesicles. Typically, the formulation of the present invention contains the weight ratio of the polymyxin to the lipid component is in the range of from about 1:20 to about 1:2.

The present invention provides methods of treating a bacterial infection in a subject by administering to the subject a pharmacologically effective amount of the liposomal formulations comprising a polymyxin or delivering the liposomal formulations via the drug delivery system described herein. The present invention provides a method for increasing efficacy of a treatment for a bacterial infection in a subject by intravenous delivery of the liposome-encapsulated polymyxin in the drug delivery system. The present invention also provides methods for delaying onset of nephrotoxicity in a subject receiving treatment or a course of treatment with polymyxin B for a bacterial infection by administering the intravenous liposomal formulation of a low dose polymyxin B with or without prior administration, for example, parenteral administration, of sodium maleate as described herein. Moreover, a method for lowering exposure to polymyxin B in renal tissues in a subject during a course of polymyxin B treatment is provided in which the low dose of polymyxin B in the intravenous liposomal formulations, with or without the sodium maleate, correlatively produces or results in a low concentration of polymyxin B in the renal tissues.

A person having ordinary skill in this art would be readily able to administer the formulations of the present invention to the subject but it is contemplated that the formulation would be administered in an amount of from about 1.5 mg/kg to about 15 mg/kg daily. Preferably, administration of the novel formulations of the present invention result in an increased polymyxin distribution into the epithelial lining fluid of the subject and increased pulmonary bioavailability and a concomittant low concentration of polymyxin in the renal tissues to thereby delay onset of nephrotoxicity.

The infective agent included in the scope of the present invention may be a microbe, for example, a bacterium that causes, but is not limited to, a pneumonia. The bacteria may be selected from *Pseudomonas aeruginosa, Acinetobacter baumannii, Klebsiella pneumoniae, Bacillus anthracis, Listeria monocytogenes, Staphylococcus aureus, Salmenellosis, Yersina pestis, Mycobacterium leprae, M. africanum, M. asiaticum, M. aviuin-intracellulaire, M. chelonei abscessus, M. fallax, M. fortuitum, M. kansasii, M. leprae, M. malmoense, M. shimoidei, M. simiae, M. szulgai, M. xenopi, M. tuberculosis, Brucella* melitensis, *Brucella suis, Brucella* abortus, *Brucella canis, Legionella pneumonophilia, Francisella tularensis, Pneumocystis carinii, mycoplasma*, and *Burkholderia cepacia*. More particularly, the bacteria is a multiple drug resistant *Pseudomonas aeruginosa, Acinetobacter baumannii*, or *Klebsiella pneumoniae*.

The property of liposomes as drug delivery vehicles is crucially dependent on their surface charge, permeability, solubility, stability etc., which is significantly influenced by the lipids comprising the liposome composition. The lipids used in the pharmaceutical formulations of the present invention can be synthetic, semi-synthetic or naturally-occurring lipids, including phospholipids, tocopherols, sterols, fatty acids, glycoproteins such as albumin, negatively-charged lipids and cationic lipids. In terms of phosholipids, they could include such lipids as egg phosphatidylcholine (EPC), egg phosphatidylglycerol (EPG), egg phosphatidylinositol (EPI), egg phosphatidylserine (EPS), phosphatidylethanolamine (EPE), and phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the number 1 position of glycerol that include choline, glycerol, inositol, serine, ethanolamine, as well as the corresponding phosphatidic acids. The chains on these fatty acids can be saturated or unsaturated, and the phospholipid may be made up of fatty acids of different chain lengths and different degrees of unsaturation.

In particular, the compositions of the formulations can include dipalmitoylphosphatidylcholine (DPPC), a major constituent of naturally-occurring lung surfactant. Other examples include dimyristoylphosphatidycholine (DMPC) and dimyristoylphosphatidylglycerol (DMPG) dipalmitoyl-phosphatidcholine (DPPQ and dipalmitoylphosphatidyl-glycerol (DPPG) distearoylphosphatidylcholine (DSPQ and distearoylphosphatidylglycerol (DSPG), dioleylphosphati-dyl-ethanolamine (DOPE) and mixed phospholipids like palmitoylstearoylphosphatidyl-choline (PSPC) and palmi-toylstearolphosphatidylglycerol (PSPG), and single acylated phospholipids like mono-oleoyl-phosphatidylethanolamine (MOPE).

The sterols can include, cholesterol, esters of cholesterol including cholesterol hemi-succinate, salts of cholesterol including cholesterol hydrogen sulfate and cholesterol sulfate, ergosterol, esters of ergosterol including ergosterol hemi-succinate, salts of ergosterol including ergosterol hydrogen sulfate and ergosterol sulfate, lanosterol, esters of lanosterol including lanosterol hemi-succinate, salts of lanosterol including lanosterol hydrogen sulfate and lanosterol sulfate. The tocopherols can include tocopherols, esters of tocopherols including tocopherol hem i-succinates, salts of tocopherols including tocopherol hydrogen sulfates and tocopherol sulfates. The term "sterol compound" includes sterols, tocopherols and the like.

The cationic lipids used can include ammonium salts of fatty acids, pholids and glycerides. The fatty acids include fatty acids of carbon chain lengths of 12 to 26 carbon atoms that are either saturated or unsaturated. Some specific examples include: myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9-(Z)-octadeceny-loxy)-prop-1-yl-N,N,N-trimethylammoniu-m chloride (DOTMA) and 1,2-bis(oleoyloxy)-3-(trimethylammonio) propane (DOTAP).

The negatively-charged lipids which can be used include phosphatidyl-glycerols (PGs), phosphatidic acids (PAs), phosphatidylinositols (PIs) and the phosphatidyl serines (PSs). Examples include DMPG, DPPG, DSPG, DMPA, DPPA, DSPA, DMPI, DPPI, DSPI, DMPS, DPPS and DSPS.

Phosphatidylcholines, such as DPPC, aid in the uptake by the cells in the lung, e.g., the alveolar macrophages, and help to sustain release of the bioactive agent in the lung. The negatively charged lipids such as the phosphatidyl-glycerols, phosphatidic acids, phosphatidylinositols and the phosphatidylserines, in addition to reducing particle aggregation, are believed to play a role in the sustained release characteristics of the inhalation formulation as well as in the transport of the formulation across the lung (transcytosis) for systemic uptake. The sterol compounds are believed to affect the release characteristics of the formulation.

Liposomes are completely closed lipid bilayer membranes containing an entrapped aqueous volume. Liposomes may be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase.

Liposomes can be produced by a variety of methods (see, e.g., Cullis et al. (1987)). Bangham's procedure (J. Mol. Biol. (1965)) produces ordinary multilamellar vesicles (MLVs). Lenk et al. (U.S. Pat. Nos. 4,522,803, 5,030,453 and 5,169,637), Fountain et al. (U.S. Pat. No. 4,588,578) and Cullis et al. (U.S. Pat. No. 4,975,282) disclose methods for producing multilamellar liposomes having substantially equal interlamellar solute distribution in each of their aqueous compartments. Paphadjopoulos et al., U.S. Pat. No. 4,235,871, discloses preparation of oligolamellar liposomes by reverse phase evaporation.

Unilamellar vesicles can be produced from MLVs by a number of techniques, for example, the extrusion of Cullis et al. (U.S. Pat. No. 5,008,050) and Loughrey et al. (U.S. Pat. No. 5,059,421)). Sonication and homogenization cab be so used to produce smaller unilamellar liposomes from larger liposomes (see, for example, Paphadjopoulos et al. (1968); Deamer and Uster (1983); and Chapman et al. (1968)).

The original liposome preparation of Bangham et al. (J. Mol. Biol., 1965, 13:238-252) involves suspending phospholipids in an organic solvent which is then evaporated to dryness leaving a phospholipid film on the reaction vessel. Next, an appropriate amount of aqueous phase is added, the 60 mixture is allowed to "swell", and the resulting liposomes which consist of multilamellar vesicles (MLVs) are dispersed by mechanical means. This preparation provides the basis for the development of the small sonicated unilamellar vesicles described by Papahadjopoulos et al. (Biochim. Biophys, Acta., 1967, 135:624-638), and large unilamellar vesicles.

Techniques for producing large unilamellar vesicles (LUVs), such as, reverse phase evaporation, infusion procedures, and detergent dilution, can be used to produce liposomes. A review of these and other methods for producing liposomes may be found in the text Liposomes, Marc Ostro, ed., Marcel Dekker, Inc., New York, 1983, Chapter 1, the pertinent portions of which are incorporated herein by reference. See also Szoka, Jr. et al., (1980, Ann. Rev. Biophys. Bioeng., 9:467), the pertinent portions of which are also incorporated herein by reference.

Other techniques that are used to prepare vesicles include those that form reverse-phase evaporation vesicles (REV), Papahadjopoulos et al., U.S. Pat. No. 4,235,871. Another class of liposomes that may be used are those characterized as having substantially equal lamellar solute distribution. This class of liposomes is denominated as stable plurilamellar vesicles (SPLV) as defined in U.S. Pat. No. 4,522,803 to Lenk, et al. and includes monophasic vesicles as described in U.S. Pat. No. 4,588,578 to Fountain, et al. and frozen and thawed multilamellar vesicles (FATMLV) as described above.

A variety of sterols and their water-soluble derivatives such as cholesterol hemisuccinate have been used to form liposomes; see specifically Janoff et al., U.S. Pat. No. 4,721,612, issued Jan. 26, 1988, entitled "Steroidal Liposomes." Mayhew et al., PCT Publication No. WO 85/00968, published Mar. 14, 1985, described a method for reducing the toxicity of drugs by encapsulating them in liposomes comprising alpha-tocopherol and certain derivatives thereof. Also, a variety of tocopherols and their water soluble derivatives have been used to form liposomes, see Janoff et al., PCT Publication No. 87/02219, published Apr. 23, 1987, entitled "Alpha Tocopherol-Based Vesicles".

The liposomes are comprised of particles with a mean diameter of approximately 0.05 microns to approximately 3.0 microns, preferably in the range about 0.5 to 1.0 microns. The sustained release property of the liposomal product can be regulated by the nature of the lipid membrane and by inclusion of other excipients, e.g., sterols, in the composition.

Considerations regarding safety and drug efficacy require that liposome formulations maintain their properties, i.e., remain stable, from the time of preparation until administration. Furthermore, it is desirable that such formulations are intact during the transport in the treated subject until they reach the target site where the drug is specifically released. While not precluding negatively charged liposomes from the instant invention, their therapeutic use may induce non-IgE-mediated hypersensitivity reactions seen in patients treated with liposomal products. These adverse reactions are thought to be a result of anaphylatoxin production through complement activation.

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 mg per kg body weight, specifically in the range of about 1 ng to about 0.1 g per kg, and more specifically in the range of about 100 ng to about 10 mg per kg. Particularly, a low dose of polymyxin, such as, but not limited to, polymyxin B comprises about 1 mg/kg to about 4 mg/kg.

An effective dose or amount, and any possible effects on the timing of administration of the formulation, may need to be identified for any particular composition of the present invention. This may be accomplished by routine experiment as described herein, using one or more groups of animals, preferably at least 5 animals per group, or in human trials, if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient, including age, sex, disease or illness type and stage, general physical condition, responsiveness to a given dosage and type of medication, route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations. Treatment may be initiated with smaller dosages that are less than the optimum dose of the compound. The dosage may be increased by small increments until the optimum therapeutic effect is attained.

The pharmaceutical formulation of the antiinfective, such as an antibacterial agent, may be comprised of either an aqueous dispersion of liposomes and free antiinfective, or a dehydrated powder containing liposomes and free antiinfective. The formulation may contain lipid excipients to form the liposomes, and salts/buffers to provide the appropriate osmolarity and pH. The dry powder formulations may contain additional excipients to prevent the leakage of encapsulated antiinfective during the drying and potential milling steps needed to create a suitable particle size for inhalation, i.e., 1-5 microns. Such excipients are designed to increase the glass transition temperature of the antiinfective formulation. The pharmaceutical excipient may be a liquid or solid filler, diluent, solvent or encapsulating material, involved in carrying or transporting any subject composition or component thereof from one organ, or portion of the body, to another organ, or portion of the body. Each excipient must be "acceptable" in the sense of being compatible with the subject composition and its components and not injurious to the patient.

Suitable excipients include trehalose, raffinose, mannitol, sucrose, leucine, trileucine, and calcium chloride. Examples of other suitable excipients include 1) sugars, such as lactose, and glucose; 2) starches, such as corn starch and potato starch; 3) cellulose, and its derivatives, such as sodium carboxymethyl cellulose, ethyl cellulose and cellulose acetate; 4) powdered tragacanth; 5) malt; 6) gelatin; 7) talc; 8) excipients, such as cocoa butter and suppository waxes; 9) oils, such as peanut oil, cottonseed oil, safflower oil, sesame oil, olive oil, corn oil and soybean oil; 10) glycols, such as propylene glycol; 11) polyols, such as glycerin, sorbitol, and polyethylene glycol; 12) esters, such as ethyl oleate and ethyl laurate; 13) agar; 14) buffering agents, such as magnesium hydroxide and aluminum hydroxide; 15) alginic acid; 16) pyrogen-free water; 17) isotonic saline; 18) Ringer's solution; 19) ethyl alcohol; 20) phosphate buffer solutions; and 21) other non-toxic compatible substances employed in pharmaceutical formulations.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Materials and Methods
Chemicals and Reagents

DPPC (1, 2-dipalmitoyl-sn-glycero-3-phosphocholine) and cholesterol were purchased from Avanti Polar Lipids (Alabaster, Ala.). Polymyxin B sulfate (USP) powder, 1.25% 2,2,2-tribromoethanol and trichloroacetic acid were purchased from Sigma-Aldrich (St. Louis, Mo.). Carbutamide was purchased from Aldrich (Milwaukee, Wis.). LC-MS grade acetonitrile and water were obtained from Mallinckrodt Baker (Phillipsburg, N.J.). LC-MS grade formic acid was purchased from Fluka Analytical (Buchs, Germany).

Polymyxin B sulfate (USP) powder was purchased from APP Pharmaceuticals LLC (lot number 6107834) (Schaumburg, Ill.) and Sigma-Aldrich (St. Louis, Mo.). Sodium maleate dibasic salt was obtained from Sigma-Aldrich. Liquid chromatography-mass spectrometry (LC-MS)-grade acetonitrile and water were obtained from Mallinckrodt Baker (Philipsburg, N.J.); LC-MS-grade formic acid was purchased from Fluka Analytical (St. Louis, Mo.). The enzyme-linked immunosorbent assay (ELISA) kit for Lrp2/megalin was purchased from Cedarlane (Burlington, N.C.).

Bacterial Strains

The multiple drug resistant (MDR) *Pseudomonas aeruginosa* strain (PA 9019) used was a bloodstream isolate from Houston, Tex. The bacterium was previously found to be resistant to all first-line agents such as anti-pseudomonal penicillins, cephalosporins, carbapenems, aminoglycosides, and quinolones (29). *P. aeruginosa* ATCC 27853 (PA 27853) was obtained from American Type Culture Collection (Rockville, Md.). The polymyxin B minimum inhibitory concentrations (MICs) for PA 9019 and PA 27853 were previously determined to be 4 mg/L and 2 mg/L, respectively.

Animals

Female Sprague-Dawley rats (225 to 250 g) (Harlan, Indianapolis, Ind.) were used. The rats received food and water ad libitum. All animals were cared for in accordance with the highest humane and ethical standards, as approved by the Institutional Animal Care and Use Committee (IACUC) of the University of Houston. The jugular veins of selected animals were cannulated to facilitate intravenous drug administration.

Preparation of Liposomal Polymyxin B Formulation

Polymyxin B was encapsulated in liposomes by a modified method of reversed-phase evaporation, followed by an extrusion. Briefly, 48 mg of polymyxin B solubilized in 12 ml of 0.1 μM phosphate buffered saline was added to a solution of 66.6 mg dipalmitoyl phosphatidylcholine (DPPC) and 11.5 mg cholesterol dissolved in 36 ml chloroform. The mixture was sonicated for 30 minutes in a water bath at 4° C. until a water-in-oil emulsion was formed. Chloroform was evaporated under pressure with a rotating speed of 100 rpm for 4 hours to remove the organic solvent and to form a uniform liposomal suspension. Finally, this liposomal dispersion was extruded through 0.8 μm polycarbonate filters (Whatman, Inc., Clifton, N.J.) using a high-pressure extruder (Northern Lipids, Inc., Canada) at 50° C. to obtain a polymyxin B liposomal formulation. Free polymyxin B was removed by centrifugation at 48,400×g for 1 h (Beckman Coulter, Indianapolis Ind.). The concentration of polymyxin B in each liposome batch was determined by a validated UPLC-MS/MS method.

Pharmacokinetic Studies

The animal protocol was approved by the University of Houston Institutional Animal Care and Use Committee. The animals received food and water ad libitum. Two groups of 24 female ND4 Swiss Webster mice (20-23 g, Harlan Laboratory, Indianapolis, Ind.) were intravenously administrated PB liposomes and aqueous solution (USP), respectively, at approximately 3 mg/kg through the tail vein. At each time point (0.1, 0.5, 1, 2, 4 and 6 h post-dose), four mice were sacrificed for blood and epithelial lining fluid sample collection. The blood samples were clotted on crushed ice and the serum was obtained by centrifugation. The epithelial lining fluid samples were obtained by bronchoalveolar lavage. All the serum and epithelial lining fluid samples were stored at −80° C. until analysis.

Serum and ELF Samples Analysis

Four major polymyxin B components in serum and epithelial lining fluid samples were assayed by a validated UPLC-MS/MS method. An Acquity UPLC HSS C18 column was used with 0.1% formic acid/acetonitrile as mobile phases. Analysis was performed in positive ionization mode with multiple reactions monitoring (MRM) scan type. Briefly, the serum and epithelial lining fluid samples (200 μl) were spiked with 20 μl of carbutamide (internal standard). Two hundred μl of 5% trichloroacetic acid was added to precipitate the proteins, followed by 1 min of vortexing. After centrifugation at 18,000× g for 15 min, the supernatant was transferred to a new tube and evaporated to dryness under a stream of nitrogen. The residue was reconstituted in 100 μl of mobile phase (acetonitrile: 0.1% formic acid=50:50) and then centrifuged at 18,000×g for 15 minutes. Ten μl of supernatant was injected into the UPLC-MS/MS for quantitative analysis. The linear concentration range was 6.5-3200 ng/ml for both serum and epithelial lining fluid samples. The intra-day and inter-day variance was less than 11 for all the components in both serum and epithelial lining fluid. The concentration of drug in epithelial lining fluid ($C_{ELF}$) was corrected using the equation: $C_{ELF}=C_{BALF} \times Urea_{serum}/Urea_{BALF}$, where $Urea_{BALF}$ and $Urea_{serum}$ were the concentrations of urea in bronchoalveolar lavage fluid (BALF) and serum, respectively (18).

Concentrations of urea in serum and BALF samples were quantified with a commercially available assay kit (Quantichrom™ Urea Assay kit, BioAssay System, Hayward, Calif.) and measured on a Synergy2 microplate reader (BioTek Instrument, Winooski, Vt.). Drug exposures observed in both serum and epithelial lining fluid were normalized by the specific dose of each batch of liposomes to account for the variances among different pharmacokinetic experiments. Naïve data averaging was used; the best-fit pharmacokinetic parameters as well as drug exposure in serum and ELF were calculated by WinNonlin 3.3 (Pharsight Corporation, Mountain View, Calif.) using a one-compartment model and non-compartmental analysis, respectively. Statistical differences between liposome and aqueous solution were determined by Mann-Whitney test at the significance level of $p \leq 0.05$.

Experimental Pneumonia Model

The animals were housed in isolation boxes to decrease the risk of infection from extraneous pathogens. To reduce the influence of innate immune function on the observed outcomes, transient neutropenia was induced using 2 doses of intraperitoneal cyclophosphamide: 150 mg/kg administered 4 days prior to infection and 100 mg/kg administered 1 day prior to infection. This procedure resulted in transient neutropenia that persisted for 1 week after the last injection (3). The animals were anesthetized by a single intraperitoneal injection of 1.25% 2,2,2-tribromoethanol at a dosage of 250 mg/kg. Overnight bacterial cultures were inoculated in cation-adjusted Mueller-Hinton broth (BBL, Sparks, Md.), grown to log phase growth and diluted to approximately $10^{4.5}$ cfu/mL (PA 9019) and $10^6$ cfu/mL (PA 27853), respectively, on the basis of absorbance at 630 nm. The bacterial inoculum selected was determined by previous lethal inoculum studies (29) and was intended to mimic a window of opportunity in which pharmacologic intervention might have an impact on patient outcomes. The bacteria were washed once in sterile saline and were inoculated (10 μL)

into the trachea of anesthetized animals under laryngoscopic guidance (29). Two hours after bacterial infection, three mice were sacrificed at baseline to ascertain the infective inoculum.

Bacterial Burden Studies

Two hours after bacterial infection, three to six mice in each treatment group were intravenously administered one of the following every 6 hours: 1) polymyxin B liposomes (3 mg/kg); 2) polymyxin B aqueous solution (3 mg/kg); 3) sham (drug-free) liposomes. The selected dosing regimen was guided by previous investigations based on the highest tolerated intravenous dose and logistic feasibility, i.e., the number of injections given via the tail vein (20). All infected mice were euthanized after 24 h by $CO_2$ asphyxiation, and lungs from each mouse were aseptically collected for quantitative culture. Prior to being cultured, the lungs were homogenized in 10 ml of sterile saline. Lung homogenate suspensions were centrifuged (10° C. at 4000×g for 15 minutes), decanted, and reconstituted with sterile saline at 10 times the original volume. The samples were subsequently serially diluted (10×) and plated on Mueller-Hinton Agar plates (Hardy Diagnostics). Colony counts were enumerated after incubation at 35° C. in a humidified incubator for 24 h. The reliable lower limit of detection was 1000 CFU/g. Statistical analysis was analyzed using the Kruskal-Wallis test. A P value 0.05 was considered to be statistically significant.

Survival Studies

Two hours after infection with PA 9019, ten mice in each treatment group were intravenously administered (0.2 mL) with either of the following every 6 h: 1) polymyxin B liposomes (3 mg/kg); 2) polymyxin B aqueous solution (3 mg/kg); or 3) sham (drug-free) liposomes for 24 h. The mice were examined every 8 h for up to 96 h. Moribund mice were humanely sacrificed at each inspection time, and death was recorded as occurred at the next inspection time. Lungs from each mouse were aseptically collected for quantitative culture as described previously, either upon death or at the end of the experiment. Survival over time was evaluated with the Kaplan-Meier analysis and log-rank test. A P value ≤0.05 was considered to be statistically significant.

Polymyxin B Assay

A validated ultraperformance liquid chromatography-tandem mass spectrometry (UPLC/MS-MS) method was modified to determine the concentrations of polymyxin B in rat serum and renal tissues, as previously described (32). The lower limit of quantification (LLOQ) was 50 ng/ml for all the major components of polymyxin B in serum as well as the renal tissue homogenate.

Correlation Between Onset of Nephrotoxicity and Renal Tissue Concentration of Polymyxin B Prior to each experiment, polymyxin B for injection (USP) was reconstituted with sterile water for injection (USP) and diluted to achieve the desired concentration. The reconstituted drug solution was stored at −80° C. in aliquots and thawed immediately before dosing.

To mimic a clinical course of polymyxin B treatment, three groups of rats (n=13 each) were administered escalating dose levels of polymyxin B (5 mg/kg, 10 mg/kg, and 20 mg/kg, respectively) once daily subcutaneously for up to 7 days. Blood samples (approximately 200 μl) were drawn via the tail vein at baseline and on a daily basis (before dosing when applicable). Blood was allowed to clot on ice, and serum was separated by centrifugation at 4,000×g for 10 min. Serum samples (100 μl) were further assayed for creatinine levels by use of a clinical chemistry analyzer (Piccolo Xpress; Abaxis, Inc., Union City, Calif.). A significant elevation in serum creatinine (≥2-fold Flow the baseline level) was set as the endpoint for nephrotoxicity. Kaplan-Meier survival analysis and a log rank (Mantel-Cox) test were used to compare the times of onset of nephrotoxicity among various groups. Right censoring was used if the nephrotoxicity endpoint was not observed by day 7.

To determine the renal tissue concentration of polymyxin B, three rats from each dosing group were randomly selected and sacrificed at 24 h after the first dose; kidneys were harvested and homogenized. A fixed time point was selected to avoid any potential confounding due to different cumulative doses received when nephrotoxocity was observed. The concentrations of the major components of polymyxin B (polymyxin B1, polymyxin B2, polymyxin B3, and isoleucine polymyxin B1) were determined in serum samples as described above.

For the purpose of drug quantification in the renal tissue homogenates, the estimated concentrations were divided by the total weight of the kidney and the final concentrations were expressed per gram of renal tissue (in micrograms/gram). The summed concentrations of individual components were used to estimate the overall renal drug exposure (33). One-way analysis of variance (ANOVA) and then post hoc Tukey's test were used to compare the mean renal tissue concentrations among the dosing groups, and P values of <0.05 were considered significant.

Effect of Maleate Administration on Megalin Homeostasis: Urinary Excretion of Megalin Three rats were housed individually in separate metabolic cages 24 h prior to maleate pretreatment. A single dose of 400 mg/kg of sodium maleate was given intraperitoneally; this was previously reported to induce reversible ultrastructural modifications in the apical brush border membrane of proximal renal tubules (34). To study megalin urinary excretion, cumulative urine was collected daily from day −1 to day 15. The urine samples were spun down to remove particulate matter. Subsequently, the urine samples were aliquoted and stored at −80° C. prior to analysis. The samples were thawed, and urinary Lrp2/megalin concentrations were quantitatively measured using a commercially available ELISA kit for megalin. For each animal, the daily megalin concentrations were expressed as a normalized ratio to the baseline megalin value.

Electron Microscopy of Maleate-Treated Kidney Sections

For morphological studies, one animal was sacrificed at 3 h and another at 14 days after maleate administration to collect the kidneys. The harvested kidneys were submitted for electron microscopic studies. Tissue samples from both renal cortical and medullary regions were fixed in 2% glutaraldehyde at 4° C. overnight, followed by additional fixation in osmium tetroxide. The renal tissue was dehydrated and embedded in epoxy resin. Approximately 1-μm pilot sections were stained with toluidine for selection of the areas for further ultrastructural examination. Thin sections of these selected areas were cut and subjected to examination under a JEOL 300 electron microscope at 80 kV. The kidneys from two naive rats were harvested, processed in a similar fashion, and used as controls.

Polymyxin B Pharmacokinetics in Megalin-Shedding Rats

To study the impact of sodium maleate pretreatment on systemic/renal exposure of polymyxin B, the rats were divided into two groups (n=13 each). Animals in both control and experimental groups were administered a single intravenous dose of 3 mg/kg of polymyxin B sulfate (USP). The intravenous route of polymyxin B administration was preferred to avoid any interference with drug absorption at the injection site. In addition, the animals in the experimental group were given 400 mg/kg of sodium maleate intraperitoneally 3 to 6 h prior to polymyxin B administration. Serum samples were obtained at 1.5, 3, 4.5, 6, and 7.5 h after polymyxin B dosing. In addition, the rats were sacrificed to harvest the kidneys at 3, 6, and 24 h (n=3 at each time point) postdosing. Polymyxin B concentrations in serum and renal tissue samples were assayed by the validated UPLC-MS/MS method detailed above.

The mean concentrations of polymyxin B in serum, as well as in renal tissue samples, at each time point were used. A modified two-compartment model (data not shown) was used to cofit the serum/renal tissue concentration-time profiles using ADAPT 5 (University of Southern California, Los Angeles, Calif.). Using the best-fit parameters, the AUC0-∞ was estimated by integrating instantaneous concentrations with respect to time. The AUC0-∞, renal tissue/AUC0-∞, serum ratio was used as an index to quantitatively assess preferential accumulation of polymyxin B in renal tissue.

To further examine whether the effect of sodium maleate on the renal accumulation of polymyxin B is transient, three additional rats were given a single dose of 400 mg/kg of sodium maleate intraperitoneally. Two weeks later, the animals were given a single dose of 3 mg/kg of polymyxin B intravenously. The rats were sacrificed at 3 h postdosing; kidneys were harvested and homogenized. Polymyxin B concentrations in renal tissue samples were assayed by the validated UPLC-MS/MS method.

EXAMPLE 2

Serum Pharmacokinetics

The concentration-time profiles (normalized by the total dose) after administration of polymyxin B liposomes and aqueous solution, respectively, are shown in FIGS. 1A-1D. All four major polymyxin B components in serum could be quantified for up to 6 hours post dose. The pharmacokinetic profiles were satisfactorily characterized by a one-compartment model. The best-fit pharmacokinetic parameters for each component are presented in Table 1. Compared with the solution group, a relatively slower clearance of all the components was found in the liposome group. However, the differences in elimination half-life and clearance were not statistically significant.

TABLE 1

Best-fit pharmacokinetic parameters of PB1, PB2, PB3 and ile-PB1 after intravenous administration of polymyxin B (n = 4)

| PK Parameters | Component | Liposome | Solution (USP) |
| --- | --- | --- | --- |
| $AUC_{0-6 h}$ (mg * h/l) | PB1 | 4.77 | 2.76 |
|  | PB2 | 1.07 | 0.30 |
|  | PB3 | 0.39 | 0.33 |
|  | ile-PB1 | 0.64 | 0.64 |
| $T_{1/2}$ (h) | PB1 | 0.60 | 0.32 |
|  | PB2 | 0.44 | 0.21 |
|  | PB3 | 0.30 | 0.28 |
|  | ile-PB1 | 0.42 | 0.29 |
| Cl (ml/h/kg) | PB1 | 444.10 | 790.06 |
|  | PB2 | 308.28 | 899.90 |
|  | PB3 | 489.78 | 664.39 |
|  | ile-PB1 | 562.65 | 575.61 |
| Vss (ml/kg) | PB1 | 382.90 | 373.06 |
|  | PB2 | 197.77 | 274.74 |
|  | PB3 | 209.87 | 267.30 |
|  | ilePB1 | 338.41 | 241.10 |

$T_{1/2}$: elimination half-life;
Cl: clearance;
Vss: volume of distribution at steady state.

EXAMPLE 3

Comparative Polymyxin B Exposures in ELF and Kidney

The epithelial lining fluid concentration-time courses of PB1, PB2, PB3 and ile-PB1 after an intravenous administration of polymyxin B liposomes and aqueous solution, respectively, are displayed in FIGS. 2A-2D. PB1 and ile-PB1 could be quantified for up to 4 h, while PB2 and PB3 could only be quantified for up to 2 h post-dose in the solution group. In contrast, all the components could be quantified up to the last sampling time point in liposome group. Drug exposures over 6 h for the liposome group was approximately 7-fold (range: 4.6 to 11.1) higher than that calculated for the solution group, as shown in Table 2. The area under the concentration-time curve $(AUC)_{0-6 h}$ was calculated from the average concentration time profile. Each time concentration was averaged by naïve pooling. Undetectable concentrations were deemed zero.

TABLE 2

Comparative epithelial lining fluid exposures of PB1, PB2, PB3 and ile-PB1 in mice after IV administration of 3 mg/kg polymyxin liposome or solution (USP) (n = 4)

| | $AUC_{0-6 h}$ (mg * h/l) | | AUC ratio |
| --- | --- | --- | --- |
| Component | Liposome | Solution | (liposome:solution) |
| PB1 | 9.75 | 1.57 | 6.21 |
| PB2 | 3.44 | 0.31 | 11.10 |
| PB3 | 1.28 | 0.26 | 4.92 |
| ile-PB1 | 2.00 | 0.44 | 4.55 |

Concomitantly, there was reduced residence of the four components in kidneys for the liposome group compared to the solution group over the 6 hours as indicated in Table 3.

TABLE 3

Comparative kidney exposures of PB1, PB2, PB3 and ile-PB1 in mice after IV administration of 3 mg/kg polymyxin liposome or solution (USP) (n = 24).

| | $AUC_{0-6 h}$ (mg * h/l) | | AUC ratio |
| --- | --- | --- | --- |
| Component | Liposome | Solution | (liposome:solution) |
| PB1 | 28.38 | 34.22 | 0.83 |
| PB2 | 9.44 | 12.24 | 0.77 |
| PB3 | 2.71 | 7.40 | 0.37 |
| ile-PB1 | 4.16 | 4.98 | 0.84 |

EXAMPLE 4

Comparative Efficacy in Neutropenic Pneumonia Model

Figure 3A:
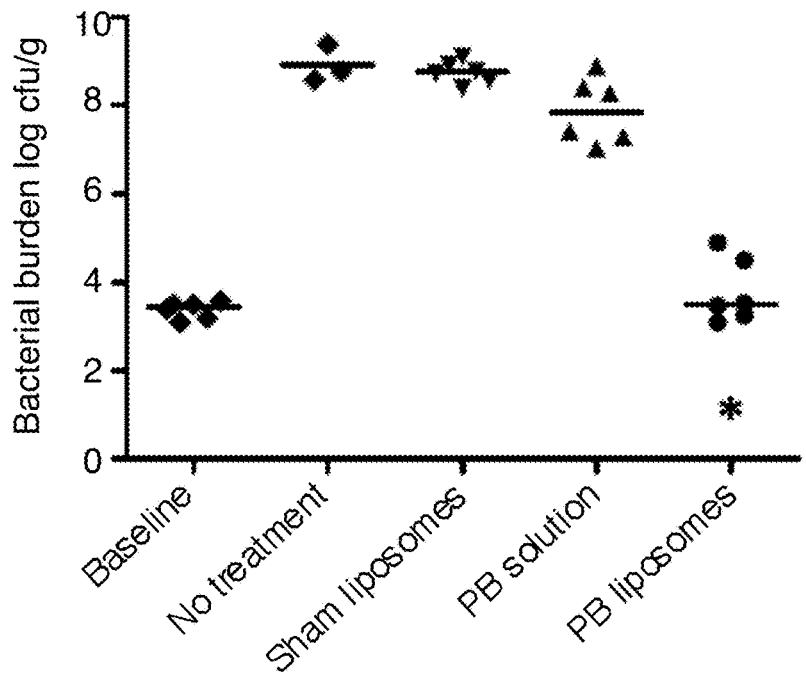
FIGS. 3A-3B shows a comparison of bacterial burden in lung tissues in PA 9010 (FIG. 3A) and PA 27853 (FIG. 3B) infected mice after 24 h of treatment with polymyxin B in solution or polymyxin B liposomes compared to no treatment and sham liposome controls. * Significantly different compared with the polymyxin B (PB) solution and sham liposomes groups (P<0.05). Each datum point represents one animal; the horizontal line in each group depicts the median bacterial burden.
Figure 3B:
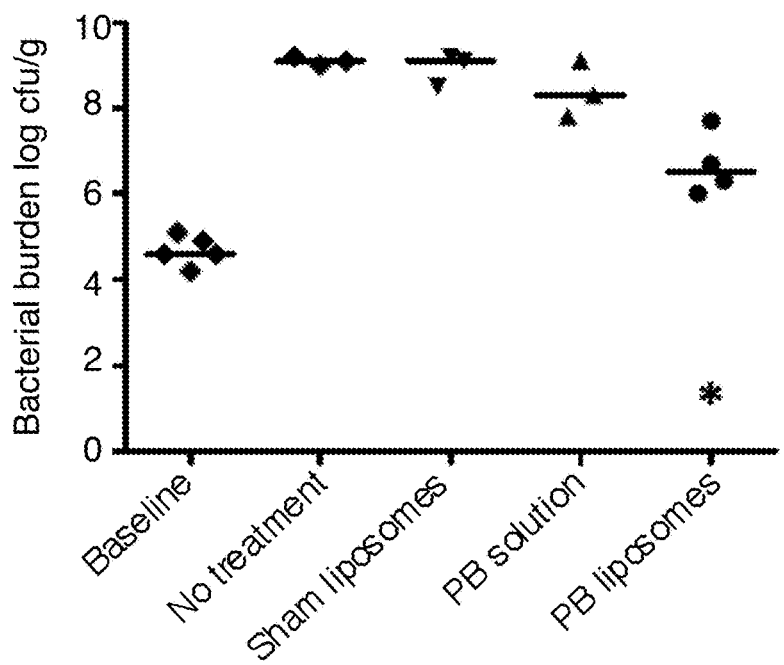

The bacterial burdens after 24 h in various treatment groups are displayed in FIGS. 3A-3B. At the start of therapy, the animals had between 3.1 to 3.6 $\log_{10}$ cfu/g (PA 9019) and 4.2 to 5.1 $\log_{10}$ cfu/g (PA 27853) in lung tissues. After 24 h, bacterial burden in lung tissues of the sham liposome control group increased to 8.4-9.1 $\log_{10}$ cfu/g (PA 9019) and 8.5-9.2 $\log_{10}$ cfu/g (PA 27853); these increases were similar to no treatment controls (P>0.05). For PA 9019, a significant difference in bacterial burden was found between the liposome group (3.8±0.7 $\log_{10}$ cfu/g) and the sham liposome control group (8.7±0.2 $\log_{10}$ cfu/g). However, only a minimal antimicrobial effect was observed in the solution group, compared to the sham liposome control group. A similar trend was observed in PA 27853.

EXAMPLE 5

Survival Studies

Figure 4:
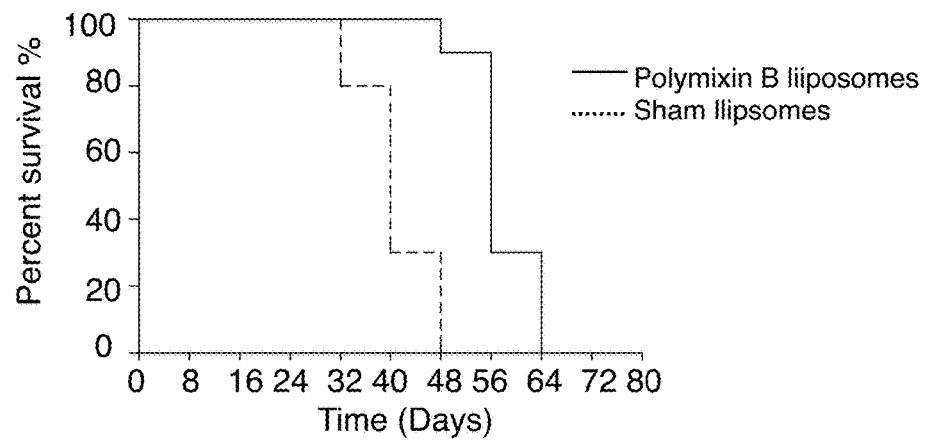
FIG. 4 shows the survival following treatment for 24 h (n=10 per group). Survival was significantly prolonged compared with the sham liposome group (P<0.001).

Therapy with liposomes for 24 h significantly prolonged the survival of animals infected with PA 9019, compared to treatment with polymyxin B solution and sham liposomes (P<0.001). In contrast, survival was not prolonged with treatment of polymyxin B solution, compared to sham liposomes. With sham liposomes treatment the median survival was 40 h, while the median survival was 44 h with treatment of polymyxin B solution and 56 h with polymyxin B liposomes (FIG. 4). In all dead animals, the tissue bacterial burdens were considerably higher (>10,000×) than baseline, suggesting pneumonia was likely the primary cause of death (data not shown). These observations were consistent with previous results of bacterial burden in lung tissues.

EXAMPLE 6

Figure 5:
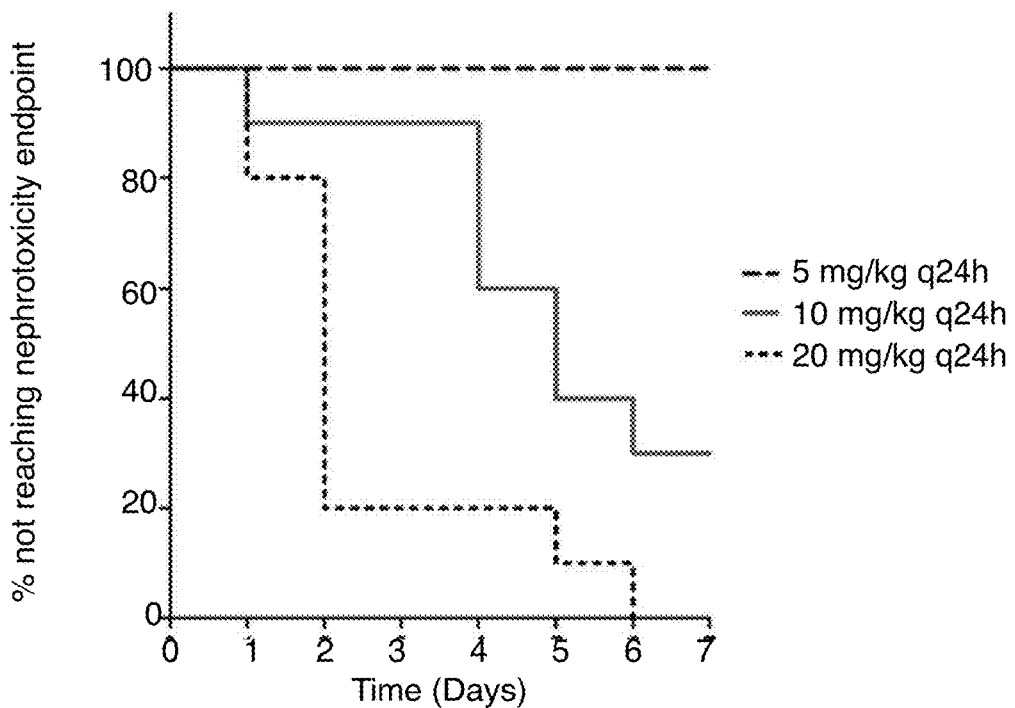
FIG. 5 shows that the onset of nephrotoxicity is dependent on daily dose. Comparison of times of onset of nephrotoxicity among different polymyxin B dosing groups (P<0.001) is shown.

Correlation Between Onset of Nephrotoxicity and Renal Tissue Concentration of Polymyxin B All of the animals (10 out of 10) that received 20 mg/kg of polymyxin B reached the predefined nephrotoxicity endpoint (i.e., a significant elevation in serum creatinine [≥2-fold the baseline level]). In contrast, none of the animals given 5 mg/kg of polymyxin B reached the endpoint by day 7. Furthermore, a more gradual onset of nephrotoxicity was observed in the 10-mg/kg group than in the 20-mg/kg dosing group, as shown in FIG. 5. More specifically, 8 out of 10 animals that received 20 mg/kg daily reached the predefined endpoint within the first 48 h of treatment. In contrast, only 1 out of 10 animals that received 10 mg/kg daily reached the endpoint within the first 48 h of treatment (P<0.001). These findings suggest that a higher daily dose of polymyxin B is associated with a more rapid onset of nephrotoxicity.

Figure 6:
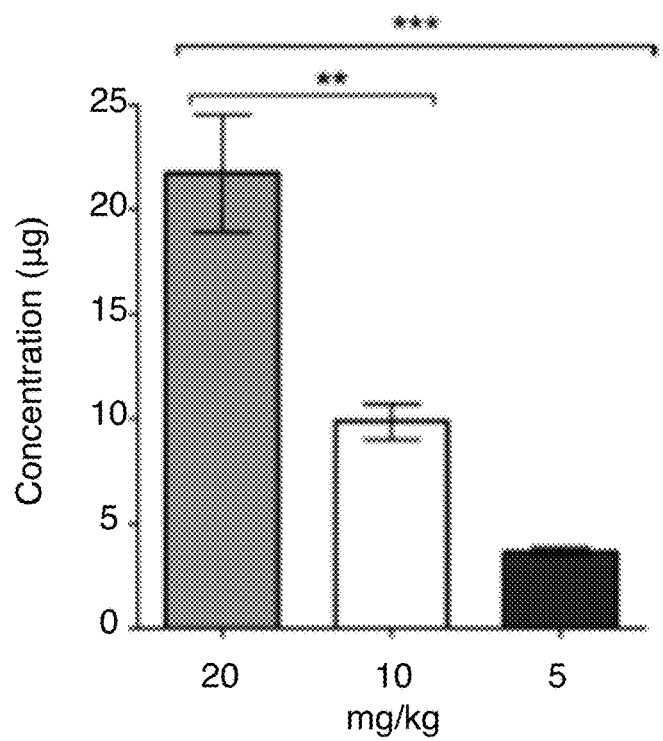
FIG. 6 shows that the daily dose is correlated to renal tissue drug concentration observed. Renal tissue concentrations at escalating dose levels of polymyxin B are shown. Vertical error bars represent the mean standard deviation within a group. The post hoc Tukey's test was used for multiple 2-way comparisons of means among different groups (*, P<0.001; , P<0.01).

A similar trend was also observed in the renal tissue concentration of polymyxin B among the various dosing groups, as shown in FIG. 6. The observed concentrations of polymyxin B in renal tissue were 3.6±0.4 µg/g, 9.9±1.5 µg/g, and 21.7±4.8 µg/g of renal tissue in the 5-mg/kg, 10-mg/kg, and 20-mg/kg dosing groups, respectively (P<0.001). These data imply that the drug concentration observed in renal tissues is also correlated with the daily dose given.

Effect of Maleate Administration on Megalin Homeostasis.

(i) Urinary Excretion of Megalin.

There was a considerable elevation (approximately 20 times the baseline measurement) in the level of urinary megalin after maleate treatment. However, the urinary megalin levels reverted gradually to baseline approximately 11 days after treatment (data not shown).

Electron Microscopy of Maleate-Treated Kidney Sections.

Figure 7A:
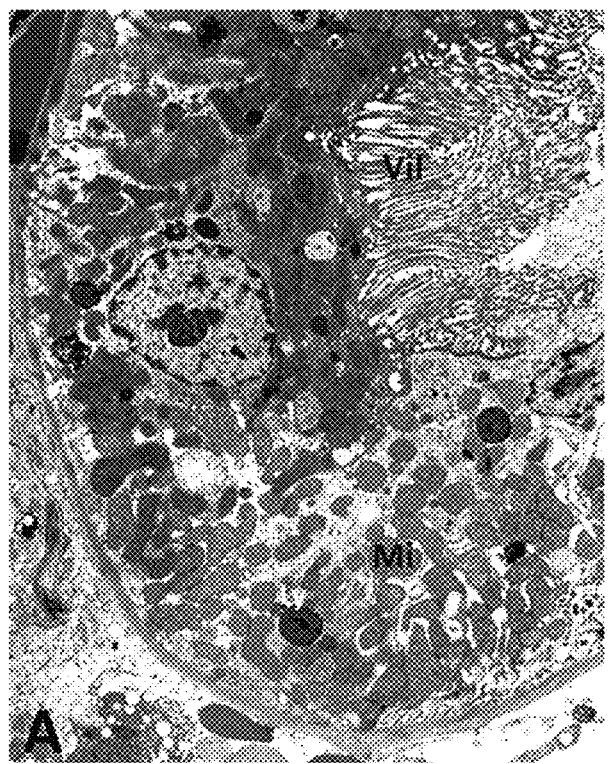
FIGS. 7A-7C show that the nephrotoxicity shown in FIG. 5 can be substantiated with histological evidence of injury.
Figure 7B:
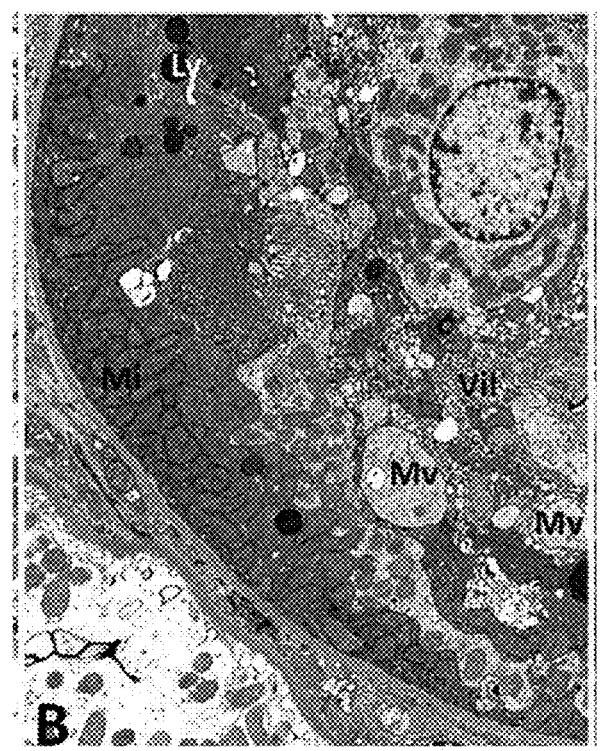
Figure 7C:
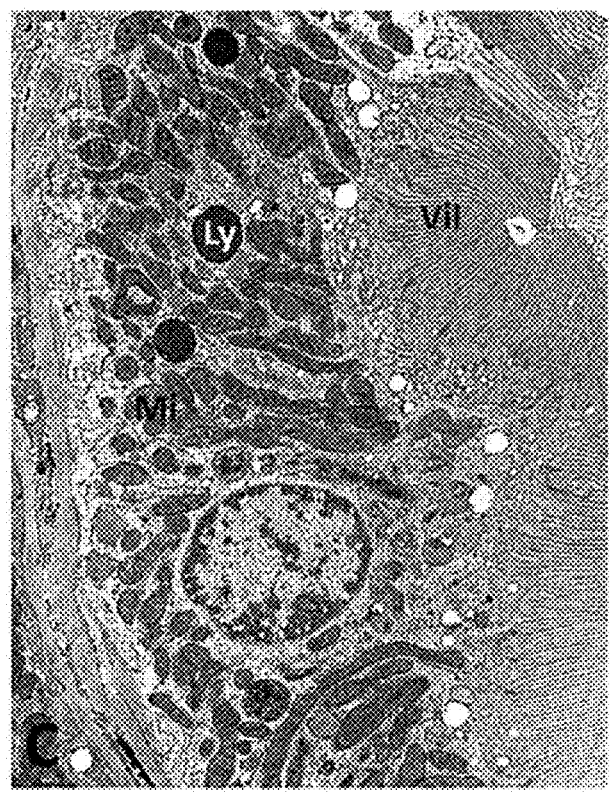

The electron microscopic images of control and maleate-treated kidney sections depict dramatic differences, as shown in FIGS. 7A-7C. No significant ultrastructural changes were noticed in the control kidney section. Specifically, the proximal tubules in control rats revealed intact microvilli, mitochondria of normal size, shape, and density, and the presence of few microvesicles and lysosomes (FIG. 7A). In contrast, within 3 h, maleate pretreatment resulted in the appearance of morphological and ultrastructural changes in the proximal tubules, including multifocal disruption of microvilli and variations in size and shape of mitochondria. The presence of multiple dilated microvesicles and abundantly enlarged lysosomes were other notable changes seen in the ultrathin sections of the maleate-treated kidney, as shown in FIG. 7B. Of note, there were no noticeable changes seen in glomeruli, blood vessels, or any other type of renal tubules. Two weeks after maleate administration, the maleate-treated kidneys revealed no significant changes (FIG. 7C). Specifically, changes attributed to maleate administration were not seen. These findings suggest that the maleate-induced renal injuries are not long-lasting and are reversible.

Polymyxin B Pharmacokinetics in Megalin-Shedding Rats

In both groups (with or without maleate pretreatment), the overall model fits with the data were satisfactory. The coefficients of determination for serum concentration-time profiles were >0.94 and for renal concentration-time profiles were >0.87. The areas under the concentration-time curve from zero to infinity for serum (AUC0-∞, serum) for the control and experimental groups were comparable, i.e., 10.4 mg·h·liter$^{-1}$ versus 11.1 mg·h·liter$^{-1}$, respectively. In contrast, the AUC0-∞ values for renal tissue (AUC0-∞, renal tissue) differed by almost 2-fold, i.e., 211.9 mg·h·liter$^{-1}$ and 121.0 mg·h·liter$^{-1}$ for the control and experimental groups, respectively, as shown in FIG. 4. The AUC0-∞, renal tissue/AUC0-∞, serum ratios were 19.1 for the control group and 11.6 for the experimental group. These findings suggest that in megalin shedding rats, the systemic exposure of polymyxin B remains unaltered but the renal exposure is reduced considerably after maleate administration.

After 2 weeks of treatment with a single dose of maleate, our results showed that renal tissue polymyxin B concentrations (3 h postdosing) in sodium maleate-pretreated rats were comparable to those of control rats (11.08 µg/g versus 11.45 µg/g, P=0.61). This finding suggests that the effect of sodium maleate on the renal accumulation of polymyxin B is also reversible in nature.

EXAMPLE 7

Discussion

With the increasing prevalence of multidrug resistance in Gram-negative bacteria, the polymyxins are increasingly used as the last viable therapeutic option against life-threatening bacterial infections. However, limited understanding of polymyxin B pharmacokinetics and underlying mechanisms of nephrotoxicity is a major hindrance to the optimal clinical use of polymyxin B.

Over the past decades, several noteworthy attempts have been made to advance the understanding of nephrotoxicity associated with the polymyxins. Suzuki et al. reported significantly diminished renal concentrations of colistin in megalin-shedding rats, which suggested the involvement of megalin in renal drug accumulation (35). A recent study by Azad et al. investigated the underlying mechanism of polymyxin B nephrotoxicity in rat (NRK-52E) as well as human (HK-2) kidney proximal tubular cell lines. Cellular apoptosis was identified to be a potential mechanism of polymyxin B-induced nephrotoxicity. It was also reported that apoptosis was triggered via activation of the caspase pathway in a time- and concentration-dependent fashion (36).

In this study, it was observed that the polymyxin B dose correlated with the renal drug concentration, and both correlated with the onset of nephrotoxicity. The higher daily dose of polymyxin B was associated with a greater degree of drug accumulation in the renal tissues, which subsequently manifested as a more rapid onset of nephrotoxicity (FIGS. 5 and 6). These findings were consistent with the previous results from the laboratory demonstrating preferential renal accumulation and prolonged residence of polymyxin B in an animal model, thereby predisposing the kidneys to the toxic effect of polymyxin B (32, 37, 38).

Additional significant findings of this study involved delineation of the possible role of an endocytic receptor (megalin or low-density-lipoprotein-related protein 2 [Lrp2]) in the renal accumulation of polymyxin B. Maleate was reported to disrupt the association of megalin with the cell membrane along the microvilli in the brush border of epithelium in renal proximal tubular cells, resulting in loss of tissue megalin and urine excretion of megalin (i.e., megalin shedding) (34, 35). In this study, it was further verified megalin shedding by the quantitative recovery of megalin in urine and the morphological examination of maleate-treated kidney sections. The electron microscopic examination of kidney sections revealed marked ultrastructural changes in the proximal tubules after maleate treatment (FIGS. 7A-7C). These results were consistent with those reported by Bergeron et al. (34). Maleate is also known to induce apical membrane-associated transport defects in the renal proximal epithelial cells similar to those observed in Fanconi syndrome. Maleate-induced ultrastructural changes transiently disrupt the apical endocytic and recycling apparatus, leading to accumulation of microvesicles in the proximal tubules (39). Therefore, the abundance of apical microvesicles in our electron microscopic study (FIGS. 7A-7C) suggests that maleate might be involved in inhibition of the membrane recycling process, thereby inducing generalized transport defects similar to those observed in Fanconi syndrome. This finding corroborated the conclusion of Christensen et al., who previously demonstrated that maleate induced inhibition of lysozyme transport from the endocytic vacuoles to the lysosomes (40). On the basis of these collective findings, it was hypothesized that megalin is involved in the internalization of polymyxin B by playing a crucial role in drug transport through the endocytic recycling apparatus. Subsequently, it was determined whether the maleate-mediated changes and the altered megalin homeostasis were reversible. Fourteen days after treatment with maleate, the initial morphological findings (including megalin shedding in the urine) were reversed to the usual pattern seen in normal rats.

It was further investigated the systemic/renal exposure of polymyxin B in megalin shedding rats. Interestingly, results indicated that polymyxin B exposure in renal tissue was attenuated by approximately 40% after pretreatment with maleate but the systemic drug exposure remained mostly unaltered in megalin-shedding rats (FIGS. 8A-8B). This could be attributed primarily to the diminished availability of membrane-bound (i.e., functional) megalin after pretreatment with maleate. These findings suggest that preferential renal accumulation of polymyxin B might be reduced by a disrupting relevant mechanism(s) of drug uptake, leading to a possible delay in the onset of nephrotoxicity.

The following references are cited herein.
1. Alipour et al., 2008. International Journal of Pharmaceutics 355:293-298.
2. Allen, T. M. 1998. Drugs 56:747-756.
3. Andes, D., and W. Craig. 1998. Antimicrob Agents Chemother 42:2375-2379.
4. Bakker-Woudenberg, I. A. 2002. International Journal of Antimicrobial Agents 19:299-311.
5. Balaji et al., 2011. Indian Journal of Medical Microbiology 29:230-242.
6. Castanheira et al., 2010. Microb Drug Resist 16:61-65.
7. Chen et al., 2009. Infectious Disease Clinics of N. America 23:1053-1075, x.
8. Coune, A. 1988. Infection 16:141-147.
9. Desai et al., 2003. Pharmaceutical Research 20:442-447.
10. Drulis-Kawa et al., 2010. International Journal of Pharmaceutics 387:187-198.
11. Fagon et al., 1996. Journal American Medical Association 275:866-869.
12. Furtado et al., 2007. Int J Antimicrob Agents 30:315-319.
13. Gales et al., 2011. The Journal of Antimicrobial Chemotherapy 66:2070-2074.
14. He et al., 2010. Int J Antimicrob Agents 35:308-310.
15. Neyland et al., 1999. Am J Respir Crit Care Med 159:1249-1256.
16. Holloway et al., 2006. Ann Pharmacother 40:1939-1945.
17. Kaye, D. 2004. Infectious Disease Clinics of North America 18:669-689, x.
18. Kiem and Schentag. 2008. Antimicrobial Agents and Chemotherapy 52:24-36.
19. Kwa et al., 2007. Expert Rev Anti Infect Ther 5:811-821.
20. Kwa et al., 2008. Diagn Microbiol Infect Dis 60:163-167.
21. McAllister et al., 1999. Journal of Antimicrobial chemotherapy 43:203-210.
22. Omri et al., 2002. Biochemical Pharmacology 64:1407-1413.
23. Orwa et al., 2001. J Chromatogr A 912:369-373.
24. Shoji et al., 1977. The Journal of Antibiotics 30:1029-1034.
25. Tam et al., 2011. Antimicrob Agents Chemother 55:4490-4491.
26. Tam et al., 2010. Antimicrob Agents Chemother 54:1160-1164.
27. Teng et al., 2008. International Journal of Antimicrobial Agents 31:80-82.
28. Tseng et al., 2012. American Journal of Infection Control.
29. Yuan et al., 2010. J Infect Dis 201:889-897.
30. Yuan, Z., and V. H. Tam. 2008. Expert Opin Investig Drugs 17:661-668.
31. Zavascki et al., 2008. Clin Infect Dis 47:1298-1304.
32. Manchandani P et al. 2016. Antimicrob Agents Chemother 60: 1029-1034.
33. Manchandani P et al. 2016. Antimicrob Agents Chemother 60:6980-6982
34. Bergeron M et al. 996. Am J Physiol 271:F908-F916
35. Suzuki T et al. 2013. Antimicrob Agents Chemother 57:6319-6324.
36. Azad M A et al. 2013. Antimicrob Agents Chemother 57:4329-4335.
37. Abdelraouf K et al. 2012. Antimicrob Agents Chemother 56:4625-4629.
38. Abdelraouf K et al. 2012. Antimicrob Agents Chemother 56:5724-5727
39. Norden A G et al. 2002. J Am Soc Nephrol 13:125-133.
40. Christensen E I et al. 1992. J Histochem Cytochem 40:1481-1490.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. The terms in the claims have their plain, ordinary meaning unless otherwise explicitly and clearly defined by the patentee.

What is claimed is:

1. An intravenous liposomal formulation, consisting of:

unilamellar vesicles each composed of lipid components dipalmitoylphosphatidylcholine and at least one of cholesterol, α-tocopherol, or phosphatidylserine at a vesicle size of about 714 nm to about 1372 nm; and a low dose of about 1 mg/kg to about 4 mg/kg of polymyxin B encapsulated in said vesicles at a weight ratio of polymyxin B to the lipid components of about 1:20 to about 1:2; for delaying onset of nephrotoxicity.

2. A pharmaceutical composition comprising the intravenous liposomal formulation of claim 1 and an intravenously acceptable excipient.

3. A method for increasing the therapeutic efficacy during treatment of a bacterial infection in a subject, comprising:

administering to the subject an amount of the intravenous liposomal formulation of claim 1 effective to decrease exposure of renal tissue to the polymyxin B during the treatment.

4. The method of claim 3, wherein administering to the subject an amount of the intravenous liposomal formulation delays the onset of nephrotoxicity.

5. The method of claim 3, wherein the bacterial infection is caused by *Pseudomonas aeruginosa, Acinetobacter baumannii, Klebsiella pneumoniae, Bacillus anthracis, Listeria monocytogenes, Staphylococcus aureus, Salmenellosis, Yersina pestis, Mycobacterium leprae, Mycobacterium africanum, Mycobacterium asiaticum, Mycobacterium aviuin-intracellulaire, Mycobacterium chelonei abscessus, Mycobacterium fallax, Mycobacterium fortuitum, Mycobacterium kansasii, Mycobacterium leprae, Mycobacterium malmoense, Mycobacterium shimoidei, Mycobacterium simiae, Mycobacterium szulgai, Mycobacterium xenopi, Mycobacterium tuberculosis, Brucella melitensis, Brucella suis, Brucella abortus, Brucella canis, Legionella pneumonophilia, Francisella tularensis, Pneumocystis carinii, mycoplasma*, or *Burkholderia cepacia.*

6. The method of claim 5, wherein the bacterial infection is caused by multiple drug resistant *Pseudomonas aeruginosa, Acinetobacter baumannii*, or *Klebsiella pneumoniae.*

7. A method for lowering exposure to polymyxin B in renal tissues in a subject during a course of polymyxin B treatment, comprising the step of:

administering to the subject the pharmaceutical composition of claim 2, wherein the low dose of polymyxin B in the pharmaceutical composition correlates to a low concentration of the polymyxin B in the renal tissues after administration, thereby lowering exposure during the course of treatment.

8. The method of claim 7, wherein lowering exposure to polymyxin B in renal tissues correlates to delaying onset of nephrotoxicity in the subject.

9. The method of claim 7, wherein the course of polymyxin B treatment is against a bacterial infection caused by *Pseudomonas aeruginosa, Acinetobacter baumannii, Klebsiella pneumoniae, Bacillus anthracis, Listeria monocytogenes, Staphylococcus aureus, Salmenellosis, Yersina pestis, Mycobacterium leprae, Mycobacterium africanum, Mycobacterium asiaticum, Mycobacterium aviuin-intracellulaire, Mycobacterium chelonei abscessus, Mycobacterium fallax, Mycobacterium fortuitum, Mycobacterium kansasii, Mycobacterium leprae, Mycobacterium malmoense, Mycobacterium shimoidei, Mycobacterium simiae, Mycobacterium szulgai, Mycobacterium xenopi, Mycobacterium tuberculosis, Brucella melitensis, Brucella suis, Brucella abortus, Brucella canis, Legionella pneumonophilia, Francisella tularensis, Pneumocystis carinii, mycoplasma*, and *Burkholderia cepacia.*

10. The method of claim 7, wherein the course of polymyxin B treatment is against a bacterial infection caused by multiple drug resistant *Pseudomonas aeruginosa, Acinetobacter baumannii*, or *Klebsiella pneumoniae.*

11. A method for delaying onset of nephrotoxicity in a subject receiving treatment with polymyxin B, comprising the step of:

administering to the subject pharmacological amounts of an intravenous liposomal formulation of a low dose of polymyxin B or pharmaceutical composition thereof effective to delay the onset of nephrotoxicity in the subject.

12. The method of claim 11, wherein the intravenous liposomal formulation consists of:

unilamellar vesicles each composed of lipid components dipalmitoylphosphatidylcholine and at least one of cholesterol, α-tocopherol, or phosphatidylserine at a vesicle size of about 714 nm to about 1372 nm; and the low dose of polymyxin B encapsulated in said vesicles at a weight ratio of polymyxin B to the lipid components of about 1:20 to about 1:2; for delaying onset of nephrotoxicity.

13. The method of claim 12, wherein the low dose of polymyxin B is about 1 mg/kg to about 4 mg/kg.

14. The method of claim 11, wherein the treatment with polymyxin B treats a bacterial infection caused by *Pseudomonas aeruginosa, Acinetobacter baumannii, Klebsiella pneumoniae, Bacillus anthracis, Listeria monocytogenes, Staphylococcus aureus, Salmenellosis, Yersina pestis, Mycobacterium leprae, Mycobacterium africanum, Mycobacterium asiaticum, Mycobacterium aviuin-intracellulaire, Mycobacterium chelonei abscessus, Mycobacterium fallax, Mycobacterium fortuitum, Mycobacterium kansasii, Mycobacterium leprae, Mycobacterium malmoense, Mycobacterium shimoidei, Mycobacterium simiae, Mycobacterium szulgai, Mycobacterium xenopi, Mycobacterium tuberculosis, Brucella melitensis, Brucella suis, Brucella abortus, Brucella canis, Legionella pneumonophilia, Francisella tularensis, Pneumocystis carinii, mycoplasma*, and *Burkholderia cepacia.*

15. The method of claim 11, wherein the treatment with polymyxin B treats a bacterial infection caused by *Pseudomonas aeruginosa, Acinetobacter baumannii*, or *Klebsiella pneumoniae.*

16. The method of claim 11, wherein delaying onset of nephrotoxicity in the subject correlates to lowering exposure to polymyxin B in renal tissues.

* * * * *